(12) United States Patent
Mullin et al.

(10) Patent No.: US 10,517,486 B2
(45) Date of Patent: Dec. 31, 2019

(54) SYSTEMS AND METHODS FOR DETERMINING PATIENT TEMPERATURE

(71) Applicant: Welch Allyn, Inc., Skaneateles Falls, NY (US)

(72) Inventors: Matthew D. Mullin, Memphis, NY (US); Matthew J. Kinsley, Marcellus, NY (US); Eric Andreassen, Syracuse, NY (US); David E. Quinn, Auburn, NY (US); Henry J. Smith, III, Auburn, NY (US); John A. Lane, Weedsport, NY (US); John Delaney, Skaneateles Falls, NY (US); Scott A. Martin, Skaneateles, NY (US); Michael J. Anson, Canton, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 15/789,233

(22) Filed: Oct. 20, 2017

(65) Prior Publication Data

US 2018/0055371 A1 Mar. 1, 2018

Related U.S. Application Data

(63) Continuation of application No. 15/017,175, filed on Feb. 5, 2016, now Pat. No. 9,795,305, which is a (Continued)

(51) Int. Cl.
*A61B 5/00* (2006.01)
*A61B 5/01* (2006.01)
(Continued)

(52) U.S. Cl.
CPC ............. *A61B 5/01* (2013.01); *A61B 5/0084* (2013.01); *A61B 5/068* (2013.01); *A61B 2034/2055* (2016.02); *A61B 2562/12* (2013.01)

(58) Field of Classification Search
CPC .................................. A61B 5/01; A61B 5/068
See application file for complete search history.

(56) References Cited

U.S. PATENT DOCUMENTS

| 3,373,611 A | 3/1968 | Trott |
| 4,343,185 A | 8/1982 | Knute |

(Continued)

FOREIGN PATENT DOCUMENTS

| EP | 721101 | 7/1996 |
| EP | 1757862 | 2/2007 |

(Continued)

OTHER PUBLICATIONS

Anal Probe with Adjustable Depth by ArtraMaples88 on Oct. 18, 2011 from gerd.goohealthlife.com, http://www.zimbio.com/Hemroids/articles/grbTA4WZUqx/Anal+Probe+Adjustable+Depth accessed: Jan. 25, 2012.

(Continued)

*Primary Examiner* — Joel F Brutus
(74) *Attorney, Agent, or Firm* — Lee & Hayes, P.C.

(57) ABSTRACT

A temperature probe includes a handle and a shaft extending from the handle. The shaft includes a distal end, a proximal end, and a tip at the distal end. The temperature probe also includes a capacitance sensor disposed on one of the handle and the shaft, the capacitance sensor configured to measure a change in capacitance when positioned proximate a conductor. The temperature probe further includes a temperature sensor disposed on the shaft, the temperature sensor configured to measure a body cavity temperature of a patient.

20 Claims, 8 Drawing Sheets

Related U.S. Application Data continuation of application No. 13/758,423, filed on Feb. 4, 2013, now Pat. No. 9,265,427, which is a continuation-in-part of application No. 13/423,785, filed on Mar. 19, 2012, now Pat. No. 9,138,149.

(51) Int. Cl.
*A61B 5/06* (2006.01)
*A61B 34/20* (2016.01)

(56) References Cited

U.S. PATENT DOCUMENTS

| | | | |
|---|---|---|---|
| 4,602,642 | A | 7/1986 | O'Hara et al. |
| 4,737,038 | A | 4/1988 | Dostoomian |
| 4,784,149 | A | 11/1988 | Berman et al. |
| 6,109,784 | A | 8/2000 | Weiss |
| 6,386,757 | B1 | 5/2002 | Konno |
| 6,647,284 | B1 | 11/2003 | Lee |
| 6,758,835 | B2 | 7/2004 | Close et al. |
| 6,789,936 | B1 | 9/2004 | Kraus et al. |
| 7,484,884 | B2 | 2/2009 | Lane et al. |
| 7,686,506 | B2 | 3/2010 | Babkes et al. |
| 8,187,270 | B2 | 5/2012 | Auth et al. |
| 2004/0170216 | A1 | 9/2004 | Russak et al. |
| 2005/0094705 | A1 | 5/2005 | Chi |
| 2006/0217618 | A1 | 9/2006 | Lia et al. |
| 2006/0293600 | A1 | 12/2006 | Wawro et al. |
| 2007/0038141 | A1* | 2/2007 | Koch ............ G01K 1/20 600/549 |
| 2007/0047618 | A1 | 3/2007 | Howanski |
| 2007/0055171 | A1 | 3/2007 | Fraden |
| 2007/0086506 | A1 | 4/2007 | Dicks et al. |
| 2007/0242726 | A1 | 10/2007 | Medero |
| 2008/0080593 | A1 | 4/2008 | Lane et al. |
| 2008/0107152 | A1 | 5/2008 | Ishimaru et al. |
| 2009/0275838 | A1 | 11/2009 | Marshall et al. |
| 2010/0113894 | A1 | 5/2010 | Padiy |
| 2010/0265986 | A1 | 10/2010 | Mullin et al. |
| 2010/0322282 | A1 | 12/2010 | Lane et al. |
| 2011/0106484 | A1 | 5/2011 | Quinn et al. |
| 2011/0118623 | A1* | 5/2011 | Nakanishi ............ G01K 13/002 600/549 |
| 2011/0130890 | A1 | 6/2011 | Tojo et al. |
| 2011/0190767 | A1 | 8/2011 | Kwan et al. |
| 2011/0216806 | A1 | 9/2011 | Weng |
| 2011/0224668 | A1 | 9/2011 | Johnson et al. |
| 2013/0023772 | A1 | 1/2013 | Kinsley et al. |
| 2016/0150975 | A1 | 6/2016 | Mullin et al. |

FOREIGN PATENT DOCUMENTS

| | | |
|---|---|---|
| JP | 2000005137 | 1/2000 |
| JP | 2000041955 | 2/2000 |
| JP | 2006308312 | 11/2006 |
| WO | WO03002966 | 1/2003 |
| WO | WO2011113727 | 9/2011 |

OTHER PUBLICATIONS

Bonds, "A Microwave Radiometer for Close Proximity Core Body Temperature Monitoring: Design, Developement, and Experimentation", University of South Florida Scholar Commons, Sep. 24, 2010, 117 pages.

"Conductive Material Thickness Measurement with Capacitive Sensors", Lion Precision, Retrieved at http://www.lionprecision.com/tech-library/appnotes/cap-0030-thickness-measurement.html, 2000, 3 pages.

Office action for U.S. Appl. No. 13/423,785, dated Jan. 17, 2014, Kinsley et al., "Systems and Methods for Determining Patient Temperature", 12 pages.

Office Action for U.S. Appl. No. 13/423,785, dated Mar. 3, 2015, Matthew J. Kinsley, "Systems and Methods for Determining Patient Temperature", 8 pages.

Office Action for U.S. Appl. No. 13/758,423, dated Apr. 24, 2015, Matthew D. Mullin, "Systems and Methods for Determining Patient Temperature", 8 pages.

Office action for U.S. Appl. No. 13/758,423, dated Aug. 12, 2015, Mullin et al., "Systems and Methods for Determining Patient Temperature", 7 pages.

Office Action for U.S. Appl. No. 13/423,785, dated Aug. 14, 2014, Matthew J. Kinsley, "Systems and Methods for Determining Patient Temperature", 17 pages.

Office action for U.S. Appl. No. 15/017,175, dated Aug. 26, 2016, Mullin et al., "Systems and Methods for Determining Patient Temperature", 13 pages.

PCT Search Report and Written Opinion dated May 16, 2014 for PCT application No. PCT/US14/14484, 12 pages.

PCT Search Report dated Jul. 15, 2013 for PCT application No. PCT/US2013/032286, 11 pages.

"Ultrasound Rectal Probe R7.5" Available at <<http://www.alibaba.com/productqs/490643023/utrasound_rectal_probe_R7_5.html>> accessed: Jan. 25, 2012.

"Vicks Baby Rectal Thermometer" Available at <<http://www.amazon.com/Vicks-V934-Baby-Rectal-Thermometer/db/B0002AHVZU>> accessed: Jan. 25, 2012.

* cited by examiner

SYSTEMS AND METHODS FOR DETERMINING PATIENT TEMPERATURE

CROSS-REFERENCE TO RELATED APPLICATIONS

The present application is a continuation of U.S. patent application Ser. No. 15/017,175, filed Feb. 5, 2016, which is a continuation of U.S. patent application Ser. No. 13/758,423, filed Feb. 4, 2013, now, U.S. Pat. No. 9,265,427, which is a continuation-in-part of U.S. patent application Ser. No. 13/423,785, now U.S. Pat. No. 9,138,149, entitled SYSTEMS AND METHODS FOR DETERMINING PATIENT TEMPERATURE, filed Mar. 19, 2012. The entire disclosure of each of the above applications is incorporated herein by reference.

FIELD OF THE INVENTION

The present disclosure relates to systems and methods for temperature determination and, in particular, to systems and methods for temperature measurement site determination.

BACKGROUND OF THE INVENTION

Measuring patient temperature is a common first step in diagnosing illnesses. Physicians commonly use a variety of methods for determining patient temperature, including, for example, obtaining temperature measurements with a thermometer. While thermometers utilizing mercury have been in existence for many years, modern thermometers typically employ one or more electronic sensors configured to measure patient temperature. Such sensors may take one or more measurements over a relatively short period of time. Based on these measurements, the thermometer may generate a predicted internal and/or core temperature of the patient. In generating this predicted temperature, it is common practice to insert at least a portion of the thermometer into a cover prior to taking temperature measurements. Known thermometers may then sense the ambient temperature of a body cavity of the patient, and may use this sensed ambient temperature in determining a patient's core temperature.

However, determining a patient's core temperature as described above can produce inaccurate results. For example, due to inherent variations in the manufacturing process, the covers utilized with such thermometers often have thicknesses that vary within a certain tolerance range. Although the variations in probe cover thickness can be a source of significant error in the core temperature determination, it can be difficult and expensive to manufacture probe covers within a relatively narrow thickness tolerance range. Thus, in an effort to minimize the effect of such error, modern thermometers may utilize algorithms that make predetermined estimates to compensate for these thickness variations. Compensating for such variations in this way may, however, introduce additional error into the core temperature determination, thereby further reducing the accuracy of such determinations.

Such thermometers are typically not configured to determine a variety of other conditions that contribute to the accuracy of the temperature determination. For instance, such thermometers are generally not configured to determine whether a probe cover has been installed thereon, or, once a probe cover has been installed, whether the installed probe cover is of an appropriate type. Additionally, such thermometers are not typically configured to determine a proximity to the body cavity or other measurement site of the patient, which measurement site is being utilized for the temperature measurement, or an insertion depth of the thermometer at the measurement site. Since known thermometers are not configured to determine such additional conditions, the algorithms utilized in the core temperature determination are limited in their sensitivity.

The exemplary embodiments of the present disclosure are directed toward overcoming the deficiencies described above.

SUMMARY

In an exemplary embodiment of the present disclosure, a temperature probe includes a handle and a shaft extending from the handle. The shaft includes a distal end, a proximal end, and a tip at the distal end. The temperature probe also includes a capacitance sensor disposed on one of the handle and the shaft, the capacitance sensor configured to measure a change in capacitance when positioned proximate a conductor. The temperature probe further includes a temperature sensor disposed on the shaft, the temperature sensor configured to measure a body cavity temperature of a patient.

In another exemplary embodiment of the present disclosure, a method of determining a core temperature of a patient includes determining a first capacitance with a capacitance sensor of a temperature probe, determining a difference between the first capacitance and a known capacitance stored in a memory associated with the temperature probe, and inserting a portion of the temperature probe into a body cavity of the patient. The method also includes measuring a body cavity temperature of the patient with the temperature probe, and calculating the core temperature of the patient based on the difference and the body cavity temperature.

In a further exemplary embodiment of the present disclosure, a temperature measurement system includes a storage container having a front, a back, at least two sides, a top, and a bottom wall disposed opposite the top. The front, back, and at least two sides are disposed orthogonal to the bottom wall, and the top includes an opening. The system also includes a conductor disposed on the bottom wall, and a plurality of probe covers disposed within the storage container and accessible for removal through the opening. A distal end of each probe cover of the plurality of probe covers contacting the conductor on the bottom wall prior to removal from the storage container.

In another exemplary embodiment of the present disclosure, a temperature probe includes a shaft having a distal end, a proximal end, and a tip at the distal end. The temperature probe also includes a first sensor disposed on the shaft. The first sensor is configured to generate a first signal indicative of at least one of a proximity to a measurement site of a patient and an identity of the measurement site. The temperature probe further includes a second sensor disposed on the shaft. The second sensor is configured to generate a second signal indicative of a temperature associated with the measurement site. The temperature probe also includes a controller in communication with the first and second sensors. The controller is configured to receive the first and second signals, and to determine a core temperature of the patient based on the first and second signals.

In an additional exemplary embodiment of the present disclosure, a method of determining a core temperature of a patient includes determining, with a first sensor, a parameter associated with a measurement site of the patient, wherein the parameter includes at least one of a change in capacitance and a change in an amount of radiation received by the first sensor. The method also includes determining at least one of a proximity to the measurement site and an identity of the measurement site based on the parameter. The method further includes determining, with a second sensor, a temperature associated with the measurement site. The method also includes determining the core temperature of the patient based on the temperature associated with the measurement site, and the at least one of the proximity to the measurement site and the identity of the measurement site.

In yet another exemplary embodiment of the present disclosure, a method of determining a core temperature of a patient includes inserting a shaft of a temperature probe into a probe cover disposed within a storage container, measuring a first change in light received by a first sensor disposed on the shaft resulting from the shaft being inserted into the probe cover, and measuring a second change in light received by the first sensor resulting from the shaft being removed from the storage container with the probe cover disposed on the shaft. The method also includes measuring a third change in light received by the first sensor resulting from the shaft and the probe cover being disposed proximate a measurement site of the patient, and measuring a temperature associated with the measurement site with a second sensor disposed on the shaft. The method further includes determining the core temperature based on the temperature associated with the measurement site, and a parameter determined based on the third change in light received by the first sensor. In such an exemplary embodiment, such a parameter may include, for example, among other things, an identity of the measurement site, a proximity to the measurement site, the presence of the probe cover on the shaft, a probe cover type, a depth of insertion of the probe at the measurement site, and/or any other like parameter.

DETAILED DESCRIPTION

Figure 1:
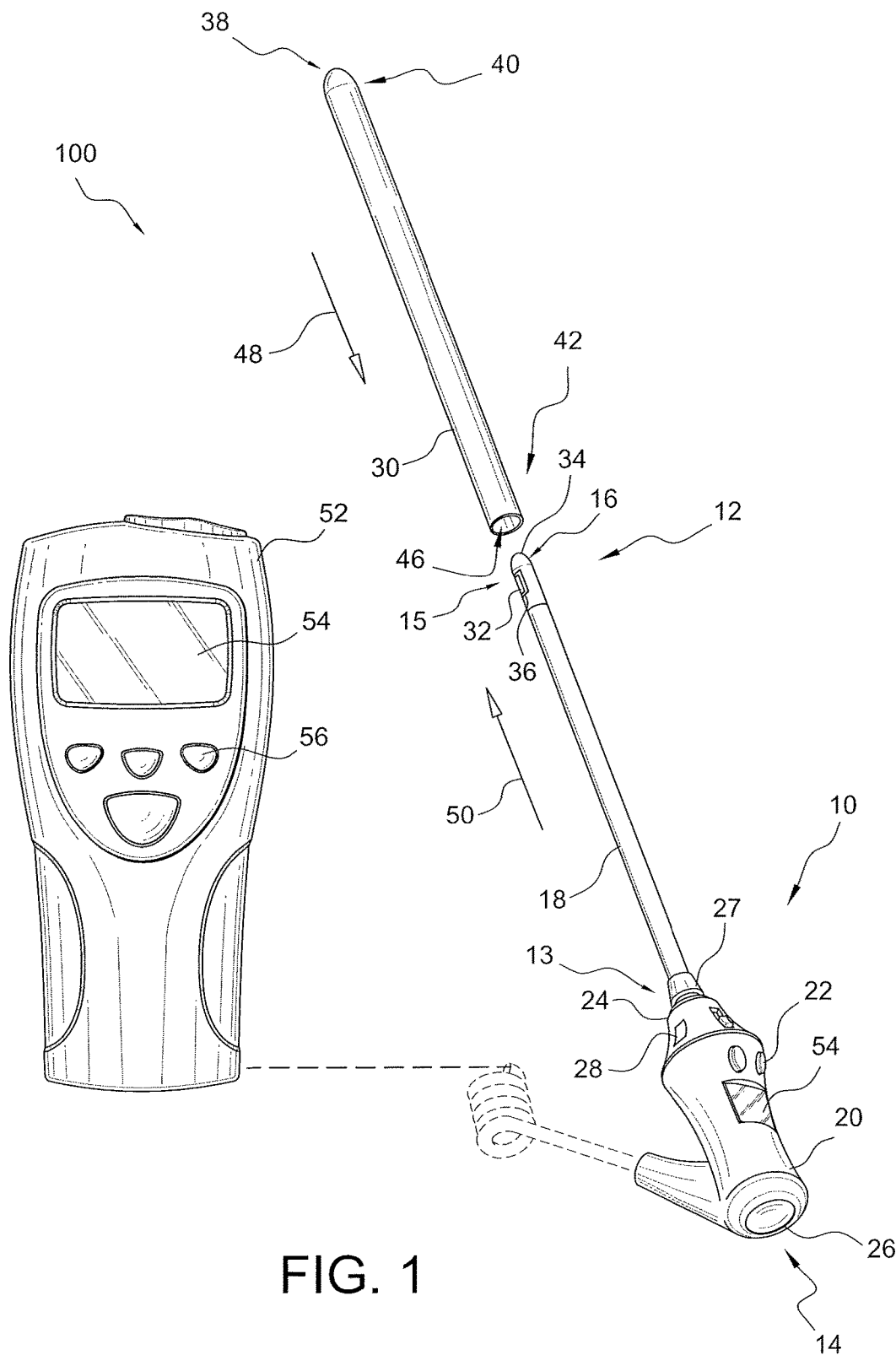
FIG. 1 illustrates a temperature probe of an exemplary temperature measurement system.

FIG. 1 illustrates an exemplary temperature probe 10 of the present disclosure. It is understood that the implementation of the disclosed technology in a temperature probe is merely exemplary. The disclosed technology may be applicable to any other probes, speculums, endoscopes, and/or other medical devices using a sheath and/or cover to protect the device from contaminants present on a surface and/or within a body cavity, where the characteristics of the sheath/cover affect the accuracy of the gathered data. Additionally, wherever possible throughout the present disclosure, like item numerals have been used to identify like components.

The temperature probe 10 may include, for example, a shaft 18 extending from a handle 20. A distal end 15 of the shaft 18 may define a distal end 12 of the temperature probe 10, and the handle 20 may define a proximal end 14 of the probe 10. The shaft 18 may also define a tip 16 disposed at the distal end 15. The tip 16 may be sufficiently rounded, atraumatic, and/or otherwise configured so as not to cause injury to a patient upon contact with a body surface and/or at least partial insertion of the shaft 18 within one or more body cavities of the patient. As used herein, the term "patient" may include any human acting to measure his/her own temperature (such as by using a temperature probe 10 without interaction from a healthcare professional), or any human or animal whose temperature is being measured. In an exemplary embodiment in which the temperature probe 10 is utilized to sense, measure, calculate, and/or otherwise determine a temperature of the patient, it is understood that such body cavities may include the mouth, rectum, axilla, ear drum, and/or other known measurement sites from which a temperature may be sensed. The shaft 18 and/or the handle 20 may be made from any material and/or combinations of materials commonly used in medical and/or examination procedures. Such materials may include, for example, plastics, polymers, composites, stainless steel, and/or any other like materials. Such materials may be suitable for repeated use and/or repeated sanitation. Accordingly, in an exemplary embodiment of the present disclosure, the temperature probe 10 and/or its components may be substantially waterproof. One or more waterproof seals may be included and/or otherwise utilized with components of the temperature probe 10 to facilitate such repeated sanitation and/or use.

The handle 20 may include one or more operator interfaces 22. Such operator interfaces 22 may be configured to assist in performing one or more functions of the temperature probe 10. For example, the operator interfaces 22 may comprise any combination of switches, buttons, levers, knobs, dials, keys, and/or other like components configured to activate, deactivate, manipulate, and/or otherwise control components of the temperature probe 10. Such operator interfaces 22 may, for example, assist the user in toggling through and/or selecting one or more modes of operation of the temperature probe 10, enabling and/or disabling one or more alarms or signals associated with operation of the probe 10, initiating a single substantially instantaneous temperature determination, initiating a substantially continuous and/or repeating temperature determination, and/or other like modes, functions, or operations.

In an exemplary embodiment, at least one of the operator interfaces 22 may comprise an ejector mechanism 26 disposed at the proximal end 14 of the temperature probe 10.

As will be described in greater detail below, at least a portion of the temperature probe 10 may be inserted into a probe cover 30 before and/or during use, and such an ejector mechanism 26 may be configured to assist in removing the probe cover 30 from the temperature probe 10. In an exemplary embodiment, actuating the ejector mechanism 26 may extend the shaft 18, in the direction of arrow 50, a desired distance from a base 24 formed at a proximal end 13 of the shaft 18. Extending the shaft 18 in this way may eject and/or otherwise remove a probe cover 30 from the shaft 18. In particular, extending the shaft 18 in the direction of arrow 50 may overcome a retention force provided by one or more shoulders, rings, tabs, extensions, and/or other like stationary retention components 27 of the temperature probe 10. Such stationary retention components 27 may be disposed, for example, proximate the base 24.

In further exemplary embodiment, the ejector mechanism 26 may be operably connected to one or more moveable components disposed at or on the base 24. In such exemplary embodiments, actuating the ejector mechanism 26 may move one or more such components in the direction of arrow 50 to assist in removing the probe cover 30 from the shaft 18. For example, such moveable components may comprise one or more fingers, hooks, shoulders, arms, tabs, rings, and/or other like moveable components configured to assist in ejecting the probe cover 30 from the base 24 of the shaft 18 after use. Such components may be movable with respect to, for example, the base 24 and/or the shaft 18, and such components may be movable in, for example, a direction substantially parallel to the shaft 18. In additional exemplary embodiments, such components may be movable in an arcuate path relative to the shaft 18. Movement of such components may assist in bending, flexing, and/or otherwise deforming at least a portion of the probe cover 30. For example, such components may be movable along one or more surfaces of the probe cover 30, and such movement may assist in flexing at least a portion of the probe cover 30. Such flexing may ultimately overcome a retention force provided by one or more of the retention components 27 described above, thereby releasing the probe cover 30 from the temperature probe 10.

In additional exemplary embodiments, one or more operator interfaces 22 may be configured to assist in controlling one or more corresponding sensors associated with the temperature probe 10. For example, the operator interfaces 22 may be operably connected to one or more sensors 32, 34, 35 disposed on the handle 20 and/or the shaft 18. For example, in the embodiment shown in FIG. 1, the operator interfaces 22 may be operably connected to first and second sensors 32, 34. Likewise, as shown in the exemplary embodiment of FIG. 11, the operator interfaces 22 may be operably connected to first sensor 32 and each of the second sensors 34. Additionally, as shown in the exemplary embodiment of FIG. 13, the operator interfaces 22 may be operably connected to first sensor 32 and each of the third sensors 35. It is understood that additional exemplary embodiments of the temperature probe 10 described herein may include any desired number and/or combination of sensors 32, 34, 35, and that one or more operator interfaces 22 may be operably connected to such sensors 32, 34, 35. In any of the exemplary embodiments described herein, the temperature probe 10 may include greater than or less than three sensors 32, 34, 35 as desired.

In exemplary embodiments, the first, second, and/or third sensors 32, 34, 35 may be embedded within and/or otherwise formed integrally with the shaft 18. In such exemplary embodiments, the sensors 32, 34, 35 may be positioned just beneath an outer surface of the shaft 18 such that the shaft 18 may retain a substantially smooth, substantially cylindrical shape. In such exemplary embodiments, it is understood that the sensors 32, 34, 35 may be electrically, operably, and/or otherwise connected to the operator interfaces 22 and/or other components of the temperature probe 10 via wireless or electrical connections embedded within and/or running along a length of the shaft 18 beneath the outer surface of the shaft 18.

In an exemplary embodiment, one or more of the sensors 32, 34, 35 may comprise any type of temperature, capacitance, optical, radiation, proximity, and/or other like sensor known in the art. For example, the sensors 32, 34, 35 may be the same type of sensor. Alternatively, the sensors 32, 34, 35 may comprise different types of sensors configured to sense one or more different characteristics of a patient. In an exemplary embodiment, at least one of the first, second, and/or third sensors 32, 34, 35 may comprise a thermocouple and/or a thermistor configured to sense a temperature associated with such a patient. For example, such a sensor may be configured to measure a temperature of the body cavity and/or other like measurement site into which the temperature probe 10 has been inserted. For example, in embodiments in which the shaft 18 of the temperature probe 10 is inserted into the mouth of the patient, such a sensor may be utilized to measure a temperature of a mouth surface. Such a sensor may also be configured to measure a temperature of the measurement site proximate to which the temperature probe 10, or a component thereof, has been disposed.

At least one of the sensors 32, 34, 35 may also comprise an infrared temperature sensor, such as, for example, a thermopile and/or other like infrared-based temperature-sensing components. Such a sensor may be configured to convert thermal energy into electrical energy, and may comprise two or more thermocouples connected in series or in parallel. Such components may be configured to generate an output voltage proportional to a local temperature difference and/or temperature gradient. In an exemplary embodiment in which the one or more of the sensors 32, 34, 35 comprise a thermopile, the temperature probe 10 may comprise, for example, an infrared temperature probe and/or other like infrared thermometer.

In such embodiments, an exemplary infrared temperature probe 10 may utilize at least a portion of the thermal radiation emitted by the patient, the body cavity, and/or the measurement site of the patient, into which the temperature probe 10 has been inserted, or proximate to which the temperature probe 10 has been disposed, in order to estimate, infer, calculate, and/or otherwise determine a core temperature of a patient temperature. Such an exemplary temperature probe 10 may utilize signals received by at least one of the sensors 32, 34, 35 to determine an amount of infrared radiation emitted by the patient. Using a known transmissivity and/or other characteristic of the patient, such infrared temperature probes 10 may be capable of determining a temperature of the patient, including a body cavity temperature of the patient and/or a core temperature of the patient.

Figure 11:
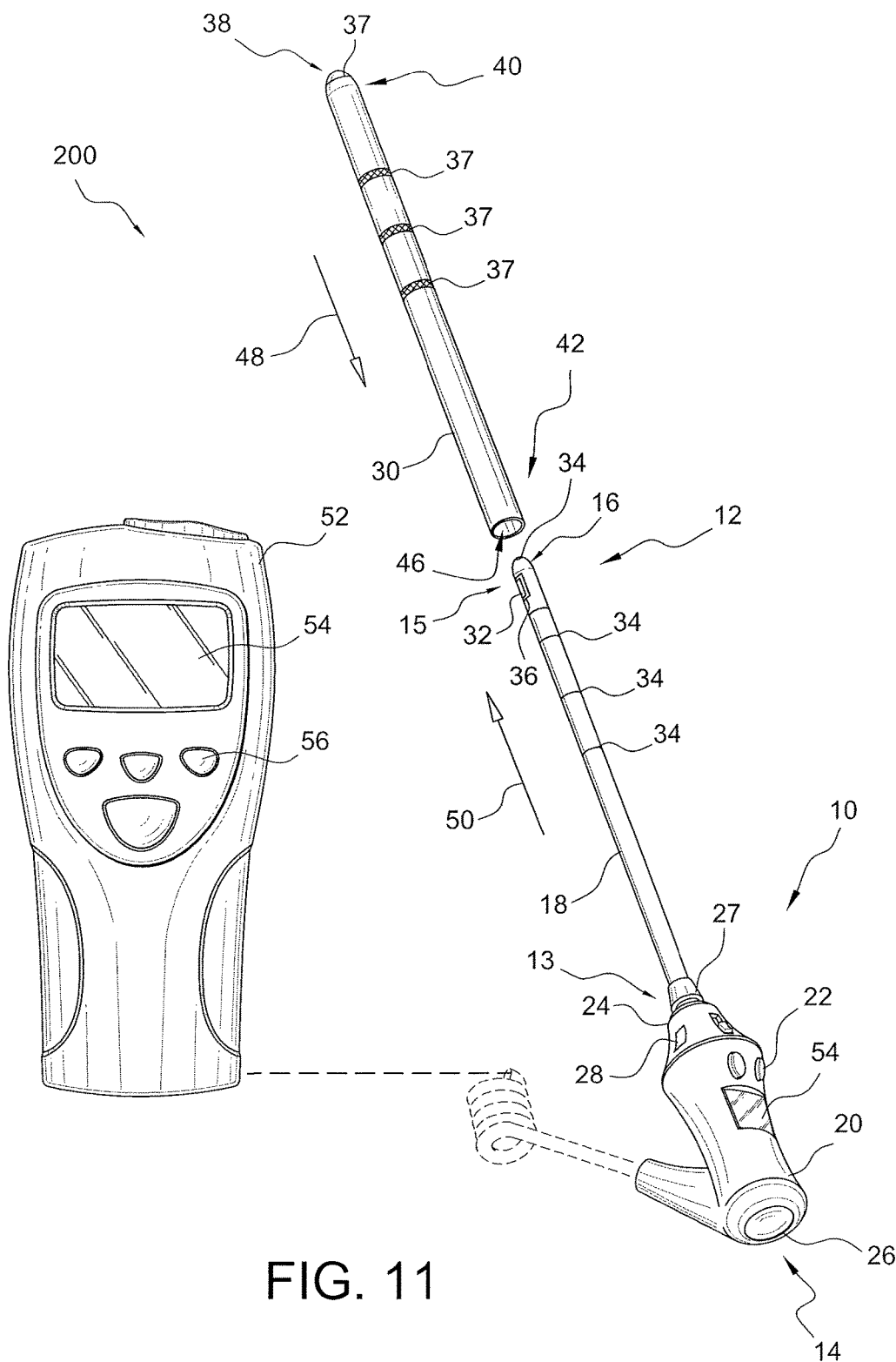
FIG. 11 illustrates a temperature probe of another exemplary temperature measurement system.

In a further exemplary embodiment, at least one of the sensors 32, 34, 35 may comprise a capacitance sensor configured to measure a capacitance and/or a change in capacitance. For example, in an embodiment in which the first sensor 32 comprises a temperature sensor, the second sensor 34 may comprise a capacitance sensor configured to measure a capacitance and/or a change in capacitance when the sensor 34 is positioned proximate a conductor. As shown in FIG. 1, in exemplary embodiments, the probe 10 may include a capacitance sensor 34 disposed proximate the distal end 15 of the shaft 18, such as, proximate the tip 16. Alternatively, as shown in FIG. 11, the probe 10 may include one or more capacitance sensors 34 disposed at various locations on and/or along the shaft 18. In the exemplary embodiment of FIG. 11, a first capacitance sensor 34 may be disposed on the shaft 18 proximate the tip 16, and at least one additional capacitance sensor 34 may be disposed on the shaft 18 proximal to the first capacitance sensor 34. In such embodiments, for example, the first capacitance sensor 34 disposed proximate the tip 16 may be configured to determine a first depth of insertion of the shaft 18 at the measurement site of the patient. Likewise, each additional capacitance sensor 34 disposed proximal to the first capacitance sensor 34 may be configured to determine respective depths of insertion greater than the first depth of insertion determined by the first capacitance sensor 34. It is understood that such respective depths of insertion may be determined by the capacitance and/or the change in capacitance determined by the one or more capacitance sensors 34. The graduated capacitance sensors 34 shown in FIG. 11 may also provide a user of the probe 10 with visual indicia of insertion depth. In the exemplary embodiment of FIG. 11, at least one of the capacitance sensors 34 may be substantially ring-shaped, and may extend around substantially an entire outer surface and/or circumference of the shaft 18. Alternatively, in additional exemplary embodiments, one or more of the capacitance sensors 34 described herein may be substantially linear. In such embodiments (not shown), the capacitance sensors 34 may extend substantially longitudinally along a length of the shaft 18. For example, such sensors 34 may extend along an outer surface of the shaft in the direction of arrow 50. Such substantially linear capacitance sensors 34 may be located at staggered and/or graduated locations along the length of the shaft 18 to provide a user of the probe 10 with visual indicia of insertion depth. Capacitance sensors 34 disposed at such graduated locations may be configured to determine respective depths of probe insertion as described above. Alternatively, such substantially linear capacitance sensors 34 may have different respective lengths. For example, a first substantially linear capacitance sensor 34 may have a first length, a second substantially linear capacitance sensor 34 disposed adjacent to the first linear capacitance sensor 34 may have a second length greater than the first length, and a third substantially linear capacitance sensor 34 disposed adjacent to the second linear capacitance sensor 34 may have a third length greater than the second length. In such embodiments, the different lengths of the respective linear capacitance sensors 34 may assist in determining different respective depths of probe insertion and may also provide a user with visual indicia of insertion depth. In each of the above embodiments, such substantially linear capacitance sensors 34 may also be employed to assist in determining the identity of the measurement site through any of the methods described herein.

The various capacitance sensors 34 described herein may comprise any type of sensor configured to detect a conductive substance or other substance having a dielectric constant different than that of air. For example, such a capacitance sensor 34 may include a first conductive layer made from copper, indium tin oxide, silver, carbon, printed ink, and/or any other known conductive material. During use, a voltage may be applied to the conductive layer, resulting in the formation of an electric field extending from the conductive layer. When a conductor is disposed within the electric field, a capacitor is formed, and the capacitance sensor 34 may measure a change in capacitance resulting from the presence of the conductor within the electric field. For example, the capacitance may change as the distance between the conductive layer of the capacitance sensor 34 and the conductor changes. The capacitance sensor 34 may be configured to generate one or more signals indicative of such a capacitance and/or such a change in capacitance, and the change in capacitance may be based on the distance between the capacitance sensor 34 and the conductor.

A variety of converters and/or other known electrical components may be used with the capacitance sensors 34 of the present disclosure to condition and/or interpret the signal generated by the capacitance sensor 34. For example, the sensors 32, 34, 35 may be operably, controllably, electrically, and/or otherwise connected to a controller 52, and such a converter may be a software and/or hardware component of the controller 52. In such an exemplary embodiment, the controller 52 may be configured to assist in calculating and/or otherwise determining a core temperature of a patient based on the temperature measurements, capacitance measurements, voltages, radiation measurements, light measurements, and/or other measurements made by the first, second, and/or third sensors 32, 34, 35. In exemplary embodiments, such converters may convert the capacitive input signals generated by the capacitance sensor 34 into digital values or "counts" representative of the measured capacitance.

As will be described in greater detail below, FIGS. 2, 5, 8, and 12 illustrate various capacitance plots of the present disclosure in which exemplary count values are shown for purposes of discussion. As exemplified by FIGS. 2, 5, 8, and 12, count value (i.e., measured capacitance) changes are based on the proximity of the capacitance sensor 34 to the conductor. For example, the measured capacitance may have its highest value (for example, 700 counts) when the capacitance sensor 34 is placed in direct contact with the conductor and no probe cover 30 is disposed on the shaft 18. Such a capacitance value may be stored within a memory of the controller 52 and may be utilized as a known reference value for determining, for example, the presence and/or absence of a probe cover 30 disposed on the shaft 18. Such a capacitance value may also be used to determine the thickness, type, and/or other characteristics of one or more probe covers 30 disposed on the shaft 18.

The measured capacitance may decrease as the conductor is spaced and/or separated from the capacitance sensor 34, such as by a probe cover 30. Thus, in further embodiments, such measured capacitance values may be used to determine a proximity of the temperature probe 10 (i.e., a proximity of the capacitance sensor 34) to a measurement site of the patient. Such proximity to the measurement site may be determined, for example, prior to contact between the shaft 18 (with or without a probe cover 30 disposed thereon) and the measurement site. For example, such a proximity to the measurement site may be determined while a probe cover 30 is disposed on the shaft 18 and prior to insertion of the shaft, or portions thereof, within a body cavity of the patient. As shown in FIGS. 2, 5, 8, and 12, the measured capacitance may vary based on the thickness of the probe cover 30 being used, and the use of a thicker probe cover 30 may result in a lower capacitance value than the use of a relatively thinner probe cover 30. Thus, such measured and known capacitance values may be used by the controller 52 to determine an unknown thickness of a probe cover 30 being used.

In still further exemplary embodiments, the capacitance sensors 34 illustrated in FIGS. 1 and 11 may be configured to determine a capacitance value and/or a change in capacitance associated with the measurement site, and the controller 52 may be configured to determine an identity of the measurement site based on one or more such values. For example, as will be described in greater detail below with respect to FIG. 12, the controller 52 may be configured to determine the identity of the measurement site (i.e., whether the measurement site comprises the mouth, the axilla, the rectum, ear drum, and/or any other like measurement site of the patient) based on a correlation between a change in capacitance measured by the one or more capacitance sensors 34 and a known change in capacitance and/or a known capacitance value associated with each respective measurement site. Such known capacitance values or change in capacitance values may be stored in, for example, a memory of the controller 52. In further exemplary embodiments, the controller 52 may be configured to determine the identity of the measurement site by, among other things, determining differences between a capacitance value, determined by one or more of the capacitance sensors 34, associated with the measurement site, and a plurality of such known capacitance values. Once such differences have been determined, the controller 52 may select one of the respective potential measurement sites of the patient corresponding to the smallest determined difference.

Figure 7:
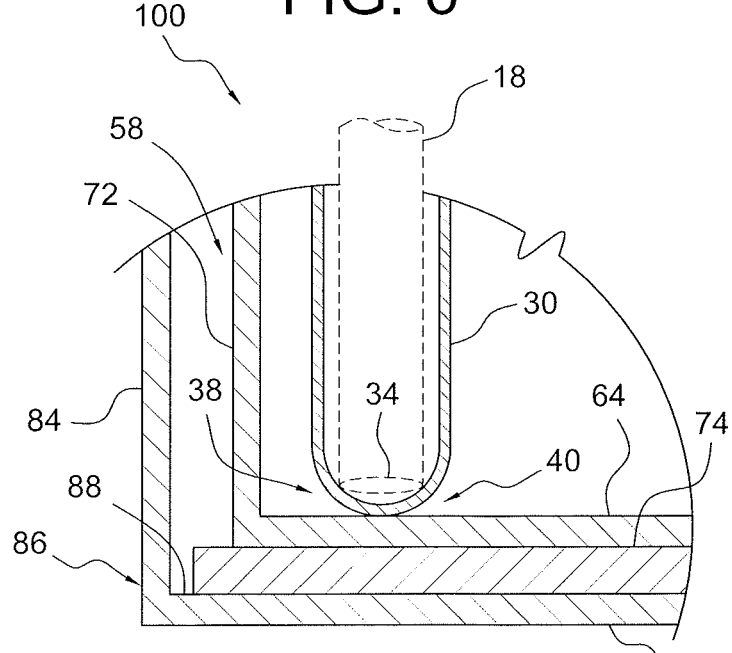
FIG. 7 illustrates a cutaway view of a portion of the user station shown in FIG. 6.

The conductors described above may comprise any conductive material and/or structure known in the art. In some embodiments, the body cavity and/or other measurement site of the patient from which a body cavity temperature is determined may be a conductor affecting the capacitance measured by the sensor 34. For example, in embodiments in which a body cavity temperature is measured by inserting the shaft 18 into the patient's mouth, the conductor may comprise the patient's tongue and/or other parts of the patient's mouth. As shown in FIGS. 4 and 7, in further exemplary embodiments, a conductor 74 may comprise a metallic sheet, film, plate, layer, coating, and/or other like structure. As will be described in greater detail below with respect to FIGS. 3 and 4, such a conductor 74 may be disposed within a storage container 58 housing one or more probe covers 30.

Figure 6:
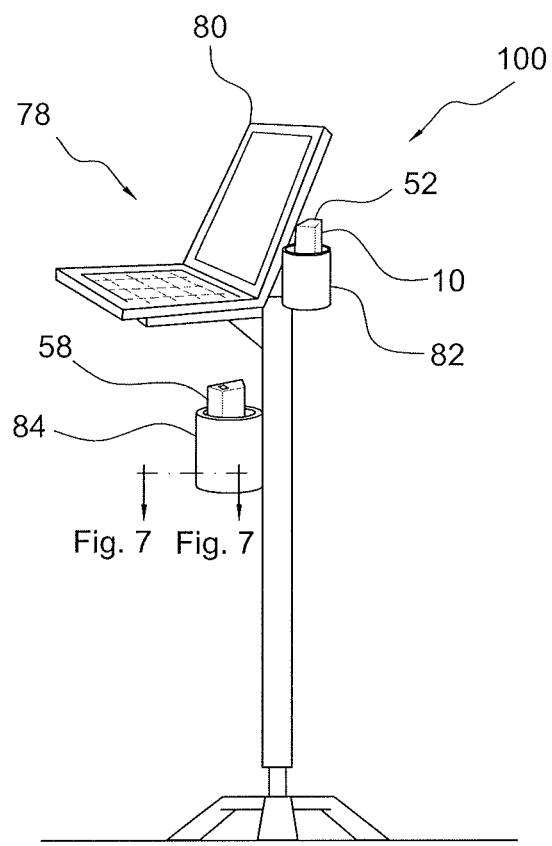
FIG. 6 illustrates a user station of an exemplary temperature measurement system.

Alternatively, in exemplary embodiments in which the storage container 58 is disposed within a receptacle 84 of a user station 78 (FIG. 6), such a conductor 74 may be disposed on a base 86 (FIG. 7) of the receptacle 84, and external to the storage container 58. Such a user station 78 may include one or more operator interfaces 80 configured for communication with the temperature probe 10 and/or the controller 52. Such a user station 78 may also include one or more additional receptacles 82 for storing the temperature probe 10 and/or the controller 52.

FIG. 7 illustrates a cutaway view of a portion of an exemplary receptacle 84 having a storage container 58 disposed therein. The receptacle 84 may include one or more walls extending orthogonal from the base 86, and the base 86 may include an inner surface 88 and an outer surface 90. Although FIG. 7 illustrates the conductor 74 being disposed on the inner surface 88, in further exemplary embodiments, the conductor 74 may be disposed on the outer surface 90 and/or on one or more of the walls extending from the base 86. In still further exemplary embodiments, the conductor 74 may be formed integrally with the base 86, and in such exemplary embodiments, the base 86 may be formed from one or more metallic and/or other conductive materials to provide the functionality of the conductors 74 described herein. Likewise, although FIG. 4 illustrates the conductor 74 being disposed on a bottom wall 64 of the storage container 58, in additional exemplary embodiments, the conductor 74 may be formed integrally with the bottom wall 64 and/or other components of the storage container 58. In such exemplary embodiments, the bottom wall 64 and/or other components of the storage container 58 may be formed from one or more metallic and/or other conductive materials to provide the functionality of the conductors 74 described herein.

Figure 9:
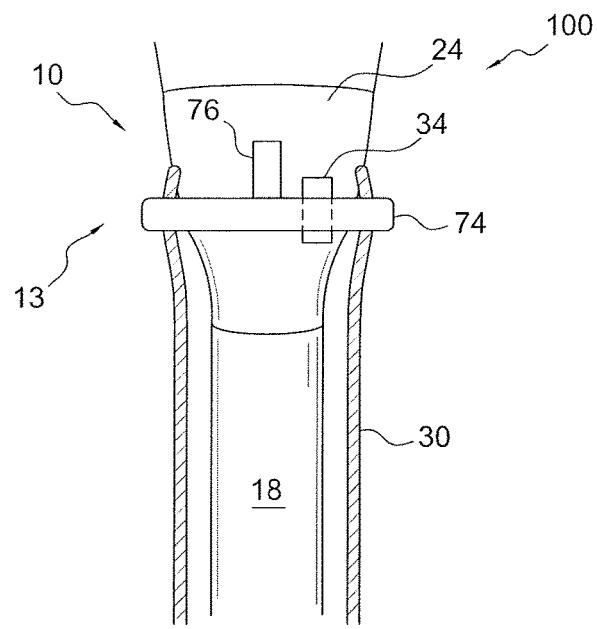
FIG. 9 illustrates a partial view of a temperature probe according to another exemplary embodiment of the present disclosure.

In still further exemplary embodiments, the conductor 74 may comprise a metallic and/or otherwise conductive ring disposed proximate the capacitance sensor 34. For example, as shown in FIG. 9, the capacitance sensor 34 may be disposed proximate the proximal end 13 of the shaft 18, and the ring-shaped conductor 74 may encircle at least a portion of the proximal end 13. In such exemplary embodiments, the conductor 74 may be connected to the temperature probe 10 in any known way, and the conductor 74 may be spaced from the outer surface of the shaft 18 such that a probe cover 30 may be disposed on the shaft 18 and/or removably connected to the shaft 18 without interference from the conductor 74. For example, such an exemplary ring-shaped conductor 74 may be connected to the handle 20 and/or the shaft 18 by one or more conductive or non-conductive mounts 76 extending from the temperature probe 10. The mount 76 may assist in spacing the conductor 74 from the outer surface of the shaft 18 such that the probe cover 30 may be disposed on the shaft 18 between the conductor 74 and a portion of the capacitance sensor 34. In such exemplary embodiments, the conductor 74 may overlay the portion of the capacitance sensor 34, and may be disposed within an electric field generated by the capacitance sensor 34 during use. Thus, disposing the probe cover 30 between the capacitance sensor 34 and the ring-shaped conductor 74 may change the capacitance value measured by the capacitance sensor 34. For example, disposing a thicker probe cover 30 on the shaft 18 between the capacitance sensor 34 and the ring-shaped conductor 74 may result in a lower measured capacitance value than the use of a relatively thinner probe cover 30.

Thus, as described above, the signal generated by the capacitance sensor 34 may be indicative of the thickness of the probe cover 30 disposed on the shaft 18 and, in particular, may be indicative of the change in capacitance sensed by the capacitance sensor 34. This change in capacitance may be based on the distance between the capacitance sensor 34 and the conductor 74. As shown in FIG. 4, this change in capacitance may result from the capacitance sensor 34 being spaced from the conductor 74 by a probe cover 30 in contact with both the distal end 15 of the shaft 18 and the conductor 74. As shown in FIG. 7, such a change in capacitance may also result from the capacitance sensor 34 being spaced from the conductor 74 by both a probe cover 30 and the bottom wall 64 of the storage container 58. Moreover, as shown in FIG. 9, such a change in capacitance may also result from the probe cover 30 being disposed between the conductor 74 and the capacitance sensor 34. Because the probe cover 30 may have a different dielectric constant than air, the probe cover 30 may attenuate the corresponding measured capacitance value.

In still further exemplary embodiments, at least one of the sensors 32, 34, 35 may comprise an optical sensor configured to determine an amount of radiation received thereby and/or a change in an amount of radiation received. For example, in an embodiment in which the first sensor 32 comprises a temperature sensor, the third sensor 35 may comprise an optical sensor configured to measure a change in an amount of radiation received by the optical sensor 35 as the sensor 35 approaches and/or is positioned proximate a measurement site of the patient. Such an optical sensor 35 may comprise, for example, a photodiode and/or any other type of like sensor configured to detect, measure, sense, and/or otherwise determine an amount of radiation received and/or a change in the amount of radiation received. It is understood that such radiation may comprise visible light and/or other radiation, such as x-ray, infrared, and/or other radiation outside of the optical band. The optical sensor 35 may be configured to generate a signal indicative of the amount of radiation received and/or the change in the amount of radiation received, and may be configured to direct such signals to the controller 52 described above. As will be described in greater detail below with respect to FIGS. 14 and 15, such signals may comprise a voltage value and/or other like value indicative of the amount of radiation received by the sensor 35.

Upon receiving one or more signals from the sensor 35, the controller 52 may be configured to determine at least one of a proximity to the measurement site and an identity of the measurement site. Additionally, the controller 52 may be configured to determine the presence of a probe cover 30 disposed on the shaft 18, and/or a probe cover type associated with the probe cover 30, based on the one or more signals. As described above, the controller 52 may be configured to assist in calculating and/or otherwise determining a core temperature of a patient based on temperature measurements made by first sensor 32 and radiation measurements made by third sensor 35. In exemplary embodiments, the controller 52 may convert the radiation input signals generated by the optical sensor 35 into voltage values representative of the amount of radiation received by the optical sensor 35 and/or the change in radiation received thereby.

Figure 14:
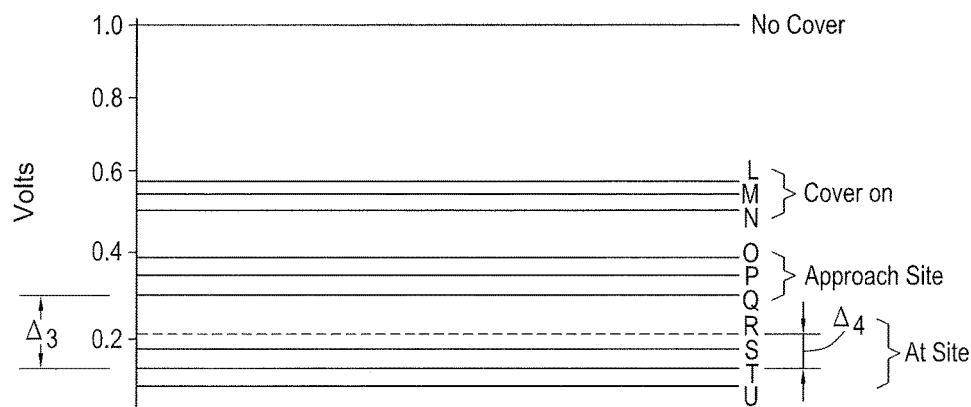
FIG. 14 illustrates an exemplary voltage plot associated with the system shown in FIG. 13.
Figure 15:
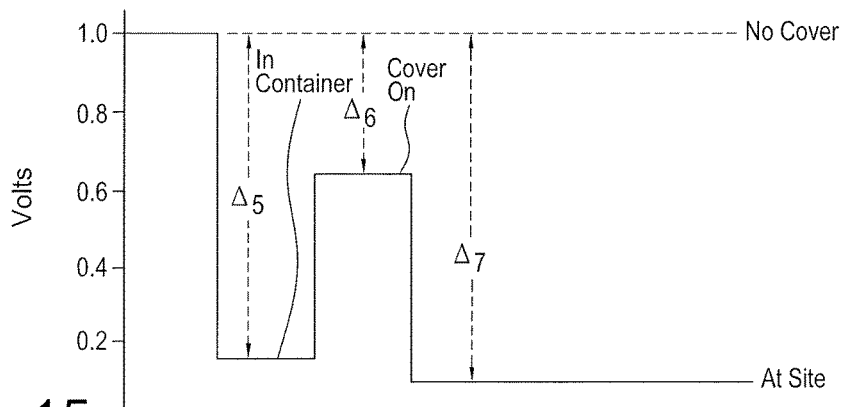
FIG. 15 illustrates another exemplary voltage plot associated with the system shown in FIG. 13.

As will be described in greater detail below, FIGS. 14 and 15 illustrate various voltage plots of the present disclosure in which exemplary voltages are shown for purposes of discussion. As exemplified by FIGS. 14 and 15, controller 52 may convert the signals received from the optical sensor 35 into corresponding voltage values indicative of the amount of radiation received by the sensor 35 at the measurement site, and changes in the amount of radiation received by the sensor 35 may correspond to changes in such voltage values. For example, the measured radiation may correspond to a relatively high voltage value (for example, 1.0 volt) when the optical sensor 35 is exposed to ambient light away from the measurement site and no probe cover 30 is disposed on the shaft 18. Such a voltage value may be stored within a memory of the controller 52 and may be utilized as a known reference value for determining, for example, the presence, type, and/or other characteristics of one or more probe covers 30 disposed on the shaft 18. Such a voltage value may also be utilized as a known reference value for determining a proximity of the probe 10 (i.e., a proximity of the optical sensor 35) to the measurement site and/or an identity of the measurement site.

At least one of the sensors 32, 34, 35 may additionally include at least one window, lens, and/or other like optical component 36 positioned proximate thereto. For example, such an optical component 36 may be disposed substantially flush and/or coplanar with the outer surface of the shaft 18. In an exemplary embodiment in which the shaft 18 is substantially cylindrical, such an optical component 36 may be substantially curved so as to match the radius of curvature of the shaft 18. Such optical components 36 may assist in, for example, focusing and/or transmitting infrared radiation between the thermopile and the body cavity of the patient. Such optical components 36 may also assist in protecting the thermopile, thermocouple, thermistor, capacitance sensor, optical sensor, photodiode, and/or other sensor components during use of the temperature probe 10, and may assist in forming a substantially fluid tight compartment within the shaft 18 so as to protect sensor components from contact with bodily fluids, cleaning solutions, and/or other liquids. It is understood that such optical components 36 may be substantially transparent to assist in the transmission of infrared radiation. Such optical components 36 may also be highly electrically and/or optically transmissive, and may have a negligible effect on, for example, an electric field generated by one or more of the sensors 32, 34, 35. Likewise, such optical components 36 may assist in transmitting visible and/or other like radiation to one or more of the sensors 32, 34, 35.

The handle 20 may also include one or more displays 54 operably connected to the controller 52. The display 54 may comprise, for example, a liquid crystal display (LCD) screen, a light emitting diode (LED) display, a digital read-out, and/or any other like components configured to communicate information to the user of the temperature probe 10. Such displays 54 may be configured to indicate, for example, one or more temperatures measured by the sensors 32, 34; 35, one or more capacitance values and/or changes in capacitance measured by the sensors 32, 34; 35, one or more values indicative of an amount of radiation received by the sensors 32, 34, 35, one or more values indicative of a change in the amount of radiation received by the sensors 32, 34, 35, one or more temperatures determined based on signals received from the one or more sensors 32, 34, 35, and/or any other information that may be useful during operation of the temperature probe 10. Such other information may include, for example, the proximity of the probe 10, and/or components thereof, to the measurement site, the depth of insertion of the shaft 18 within the measurement site, and the identity of the measurement site. The display 54 may be configured to communicate such information substantially instantaneously and/or substantially continuously, depending on the mode of operation of the temperature probe 10. Such a display 54 may also indicate whether or not the temperature probe 10 is turned on and whether a probe cover 30 has been connected to the temperature probe 10. The display 54 may also be configured to indicate the mode of operation of the temperature probe 10 (for example, continuous or instantaneous modes of temperature calculation), as well as whether one or more threshold temperatures, threshold temperature change rates, and/or other sensed metric thresholds have been met or exceeded. The display 54 may be, for example, a substantially numerical digital display, and may also be configured to display any other typical operating information, such as, for example, a temperature versus time trend line or other graphical depictions. Such graphical depictions may also include one or more capacitance plots of the type illustrated in FIGS. 2, 5, 8, and 12.

The temperature probe 10 may also include one or more signal devices (not shown) operably connected to the controller 52. Such signal devices may include, for example, one or more lights, LEDs, speakers, and/or other like devices configured to emit an audible and/or optical alarm or signal in response to a command or signal from the controller 52. Such an alarm or other signal may be initiated by, for example, the controller 52 when the calculated temperature meets or exceeds a threshold temperature. Such an alarm and/or other signal may also be initiated by the controller 52 based on a determined proximity to the measurement site, a depth of insertion, an identity of the measurement site, and/or other determinations made by the controller 52. For example, such alarms or other signals may be initiated in response to meeting or exceeding one or more predetermined thresholds associated with such determinations. In additional exemplary embodiments, such an alarm or signal may be initiated during a substantially continuous temperature calculation operation where the rate of patient temperature change meets or exceeds a predetermined temperature change rate threshold. In additional exemplary embodiments, such signal/devices may be disposed on and/or otherwise associated with the controller 52.

The controller 52 may be operably connected to the operator interfaces 22, display 54, sensors 32, 34, 35, and/or other components of the temperature probe 10, and the controller 52 may be configured to control the operation of such components. In an exemplary embodiment, the controller 52 may be configured to receive signals, information, measurements, and/or other data from the sensors 32, 34, 35 of the temperature probe 10, and to estimate, calculate, and/or otherwise determine a core temperature of the patient based on the information received. The controller 52 may also be configured to execute one or more commands and/or control programs. For example, the controller 52 may be programmed to initiate one or more alarms in response to calculating a core temperature that is greater than or equal to a predetermined threshold temperature. In an exemplary embodiment, such a threshold temperature may be approximately 100° F. In addition, the controller 52 may be configured to initiate such an alarm during a substantially continuous temperature calculation operation if the calculated temperature increases and/or decreases at a rate that is greater than or equal to a predetermined threshold temperature change rate. The controller 52 may comprise a processor, memory, and/or other known controller components to facilitate the functionality described herein.

Figure 12:
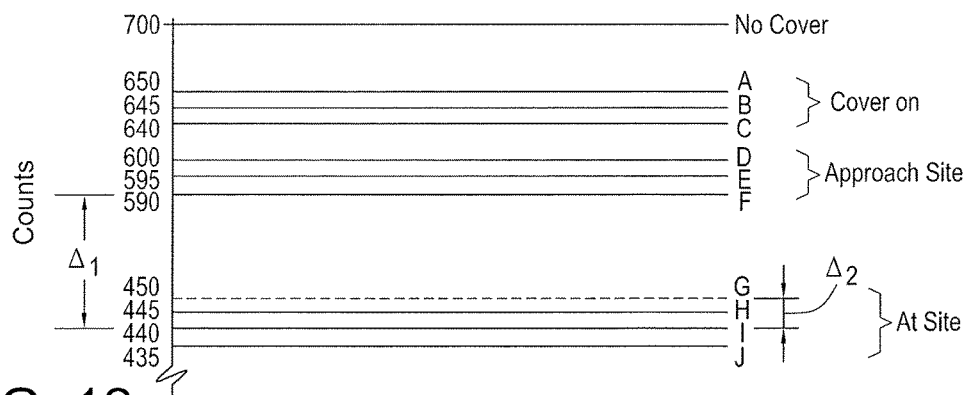
FIG. 12 illustrates an exemplary capacitance plot associated with the system shown in FIG. 11.

In an exemplary embodiment, the controller 52 may be disposed within, for example, the handle 20 of the temperature probe 10. In such an embodiment, the controller 52 may be formed substantially integral with the temperature probe 10. For example, the handle 20 may form one or more substantially watertight and/or substantially hermetically sealed compartments for storing the various components of the controller 52. Alternatively, as shown in FIGS. 1, 11, and 12, the controller 52 may be formed separately from the temperature probe 10. In such exemplary embodiments, the controller 52 may comprise a housing that is formed separate from the handle 20. To facilitate communication between the temperature probe 10 and the controller 52 in such embodiments, the controller 52 may be operably connected to the temperature probe 10 via one or more wires, cables, USB connection, Bluetooth, WiFi, radio, and/or other known hard-wired and/or wireless communication protocols. The controller 52 and/or the temperature probe 10 may further include any number of ports, connectors, transponders, receivers, antennae, and/or other known components to facilitate such connectivity and/or communication. As shown in FIG. 1, in an exemplary embodiment in which the controller 52 is formed separate from the temperature probe 10, the controller 52 may comprise a display 54 and one or more operator interfaces 56. The display 54 and operator interfaces 56 of the controller 52 may be structurally and/or functionally similar to the display 54 and operator interfaces 22 of the handle 20 described herein.

The probe cover 30 may be substantially cylindrical, and may have similar dimensions to that of the shaft 18. For example, the probe cover 30 may be incrementally longer than the shaft 18 so as to fit over substantially the entire shaft 18. The probe cover 30 may define an orifice 46 at a proximal end 42 thereof. Similar to the shaft 18, the probe cover 30 may also define a substantially atraumatic tip 38 at a distal end 40 thereof. The probe cover 30 may be formed from any medically approved material known in the art. Such materials may include, for example, plastics, polymers, and/or any of the other materials discussed above with regard to the temperature probe 10. Using such materials may enable, for example, the probe cover 30 to be repeatedly used and/or sanitized. Alternatively, in additional exemplary embodiments, the probe cover 30 may be configured for one-time usage. In exemplary embodiments, the probe cover 30 and/or portions thereof may function as an optical filter. In such embodiments, portions of the probe cover 30 may be tinted, textured, shaped, dimensioned, and/or otherwise configured to modify light and/or other radiation passing through the probe cover 30. In such embodiments, the portions of the probe cover 30 functioning as an optical filter may assist in collimating, focusing, and/or otherwise directing radiation passing through the probe cover 30. For example, such portions of the probe cover 30 may be configured to assist in maximizing the amount of radiation passing through the probe cover 30, and on to the one or more sensors 32, 34, 35. In this way, such portions of the probe cover 30 may improve the functionality of such sensors sensors 32, 34, 35.

In additional exemplary embodiments, the probe cover 30 may include one or more additional structures to facilitate usage with, insertion on, and/or removal from the temperature probe 10. For example, while the orifice 46 may be shaped, sized, and/or otherwise configured to accept the shaft 18 and to mate with one or more retention components 27 of the temperature probe 10, in further exemplary embodiments, at least a portion of the proximal end 42 of the probe cover 30 may include additional notches, cutouts, tabs, ribs, rings, flanges, and/or other retention components (not shown) configured to assist in connecting the probe cover 30 to and/or disconnecting the probe cover 30 from the temperature probe 10. For example, such retention components of the probe cover 30 may mate with the retention components 27 of the temperature probe 10 to facilitate retention of the probe cover 30 on the shaft 18 and/or ejection of the probe cover 30 from the shaft 18.

Figure 13:
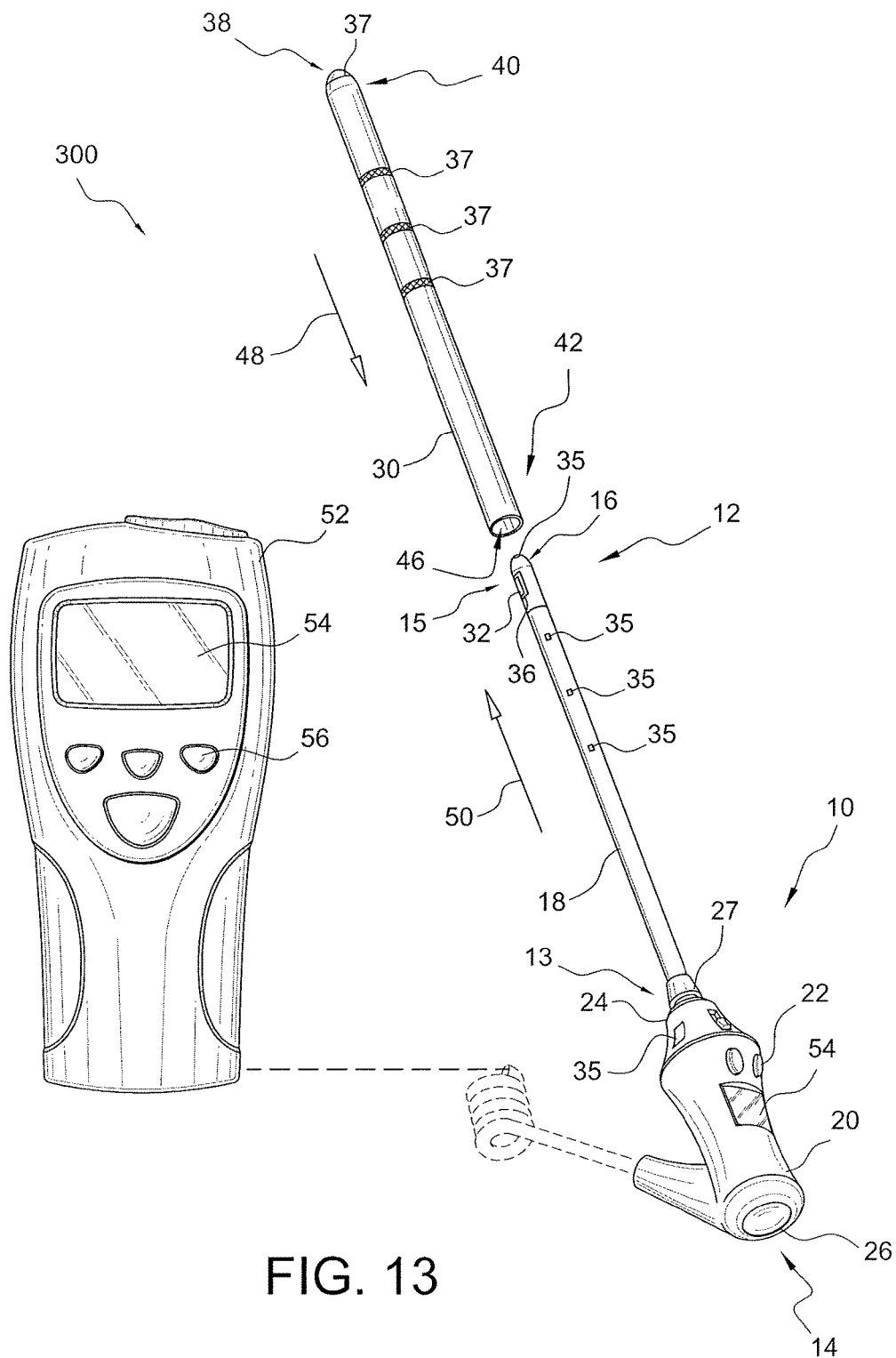
FIG. 13 illustrates a temperature probe of further exemplary temperature measurement system.

As shown in FIGS. 11 and 13, exemplary embodiments of the probe cover 30 may also include one or more features 37 shaped, sized, located, and/or otherwise configured to facilitate operation of the one or more sensors 32, 34, 35. For example, such features 37 may comprise windows, lenses, and/or other like structures configured to facilitate passage of radiation to a respective optical sensor 35, emission of an electrical field by a respective capacitance sensor 34, and/or transmission of thermal energy to a temperature sensor 32. In each of the exemplary embodiments described herein, one or more of the features 37 may comprise a groove, channel, trough, notch, cut-out, and/or other like structure. In exemplary embodiments in which the temperature sensor 32 comprises an infrared temperature sensor, such features 37 may be configured to facilitate passage of infrared radiation to and from such a temperature sensor 32. In additional exemplary embodiments, the features 37 may comprise a portion of the probe cover 30 that has been removed by laser etching, cutting, and/or other like methods. In still further embodiments, the features 37 may comprise a portion of the probe cover 30 having a wall thickness that is less than surrounding portions and/or a remainder of the probe cover 30. In such embodiments, the features 37 may be formed during the probe cover molding, extrusion, and/or other manufacturing process. For example, the features 37 may be formed into one or more of the molds used to manufacture the probe cover 30.

As shown in FIGS. 11 and 13, the location of each feature 37 on the probe cover 30 may correspond to the location of a respective one of the sensors 32, 34, 35 on the shaft 18, such that when the probe cover 30 is disposed on the shaft 18, each feature 37 may be disposed proximate and/or substantially over a respective one of the sensors 32, 34, 35. In each of the exemplary embodiments described herein, one or more of the features 37 may comprise a groove, channel, trough, notch, cut-out, and/or other like structure.

In further exemplary embodiments, at least one of the features 37 may be configured to modify radiation passing to a respective optical sensor 35, an electrical field emitted by a respective capacitance sensor 34, and/or thermal energy transmitted to a temperature sensor 32. For example, in embodiments in which a feature 37 is disposed proximate and/or substantially over a capacitance sensor 34, the feature 37 may be configured to intensify, focus, direct, and/or otherwise affect the electrical field emitted by the capacitance sensor 34. Such a feature 37 may also be configured to enhance a sensitivity of the sensor 34, thereby improving the capability of the sensor 34 to determine a capacitance and/or a change in capacitance at the measurement site.

In additional exemplary embodiments, at least one of the features 37 may be sized, shaped, located, and/or otherwise configured to assist in determining the identity of the measurement site. For example, one or more of the features 37 may be dimensioned such that portions of the patient's anatomy found at a first measurement site may interact with the feature 37 differently than portions of the patient's anatomy found at a second measurement site. Such interaction may have a unique effect on the signals sent by a respective sensor 32, 34, 35 disposed beneath such a feature, and the controller 52 may be configured to determine the identity of the measurement site based at least in part on such an effect. For example, at least one of the features 37 may comprise one or more longitudinal, radial, and/or other like grooves. In such an embodiment, a patient's tongue may be compliant enough to at least partially conform to and/or otherwise fill such grooves, while portions of the axilla and/or rectum may not be as compliant. Accordingly, the interaction between the patient's tongue and such a feature 37 may affect the capacitance and/or change in capacitance determined by a respective capacitance sensor 34 disposed beneath such a feature 37. For instance, such interaction may augment the capacitance and/or change in capacitance determined by the capacitance sensor 34 disposed beneath such a feature 37 by a known amount and/or in any other known way. Accordingly, the controller 52 may be configured to determine, among other things, the identity of the measurement site (i.e., that the capacitance sensor 34 and/or the shaft 18 of the temperature probe 10 is disposed at or in the patient's mouth) based on signals received while using a probe cover 30 having such features 37. Although such measurement site identity determinations have been described above with respect to a capacitance sensor 34, in further exemplary embodiments, similar proximity and/or measurement site identity determinations may be made using such features 37 in conjunction with one or more of the temperature sensors 32, optical sensors 35, and/or other sensors described herein. In each of the exemplary embodiments described herein, such features 37 may be shaped, sized, located, and/or otherwise configured such that epidermal and/or other tissue of the patient may fit within at least a portion of one or more such features 37 to aid in determining the identity of the measurement site, the proximity to the measurement site, the temperature of the measurement site, and/or any of the other measurement site characteristics described herein.

In a similar manner, interaction between such features 37 and respective sensors 32, 34, 35 may assist the controller 52 in determining the type of probe cover 30 being used. For instance, such interaction may have a unique effect on the signals sent by a respective sensor 32, 34, 35 disposed beneath such a feature, and the controller 52 may be configured to determine the probe cover type and/or the probe cover manufacturer based at least in part on such an effect. In exemplary embodiments, one or more such features 37 may be shaped, sized, located, and/or otherwise configured to be indicative of the particular type and/or manufacturer of the probe cover 30. In such embodiments, the controller 52 may be configured to determine whether the probe cover 30 being used is, for example, of an approved probe cover type and/or from an approved probe cover manufacturer based on signals received from respective sensors 32, 34, 35 indicative of the characteristics of such features 37. The controller 52 may also be configured to take further action based on such determinations. In exemplary embodiments, the controller 52 may be configured to permit activation and/or use of one or more of the sensors 32, 34, 35 in response to determining that the probe cover 30 is of an approved type and is from an approved probe cover manufacturer. On the other hand, the controller 52 may be configured to disable one or more components of the temperature probe 10 in response to determining that either the probe cover 30 is not of an approved type or that the probe cover 30 is not from an approved probe cover manufacturer.

In still further exemplary embodiments, one or more additional sensors 28 may be disposed on the temperature probe 10 at a location useful for detecting the presence of the probe cover 30. For example, such sensors 28 may be disposed proximate the base 24 of the shaft 18 and configured to detect the proximal end 42 of the probe cover 30 once the shaft 18 has been inserted into the probe cover 30. In still further exemplary embodiments, such sensors 28 may be disposed proximate the tip 16 and configured to detect the distal end 40 of the probe cover 30 once the shaft 18 has been inserted into the probe cover 30. In such exemplary embodiments, the one or more sensors 28 may comprise, for example, a proximity sensor and/or any other like sensing device, and sensing the first temperature indicative of a temperature of the probe cover 30 may be performed in response to detecting the presence of the probe cover 30 on the shaft 18. As shown in the exemplary embodiment of FIG. 13, in additional exemplary embodiments, such an additional sensor may comprise an optical sensor 35 disposed on the temperature probe 10 such that the optical sensor 35 is exposed to ambient light and/or other ambient conditions outside of the probe cover 30 when the probe cover 30 is disposed on the shaft 18. Such an optical sensor 35 may be disposed on and/or proximate to, for example, the base 24 of the shaft 18.

The exemplary temperature measurement systems 100, 200, 300 of the present disclosure, shown in FIGS. 1, 11, and 13, respectively, may include any of the temperature probes 10, controllers 52, and/or probe covers 30 described herein, as well as the various components thereof. In addition, exemplary temperature measurement systems 100, 200, 300 of the present disclosure may further include a storage container 58 (FIGS. 3, 4, 6, and 7), and as mentioned above, one or more probe covers 30 may be disposed within the storage container 58. The storage container 58 may have any shape, size, and/or other configuration convenient for storing a plurality of probe covers 30 therein. For example, the storage container 58 may be substantially box shaped, and may have a substantially rectangular, substantially square, and/or substantially hexagonal cross-sectional shape.

At least a portion of the storage container 58 may define one or more openings 60. Such exemplary openings 60 may be shaped, sized, located, and/or otherwise configured to assist in the removal of one or more probe covers 30 from the storage container 58. For example, such an opening 60 may be shaped and/or sized to permit passage of a probe cover 30 for removal from the storage container 58. Such an opening 60 may also be shaped and/or sized to permit removal of only a single probe cover 30 from the storage container 58 at one time. In such an exemplary embodiment, the opening 60 may assist in retaining the remaining probe covers 30 within the storage container 58 while, at the same time, facilitating removal of a single probe cover 30 for use with the temperature probe 10.

Figure 3:
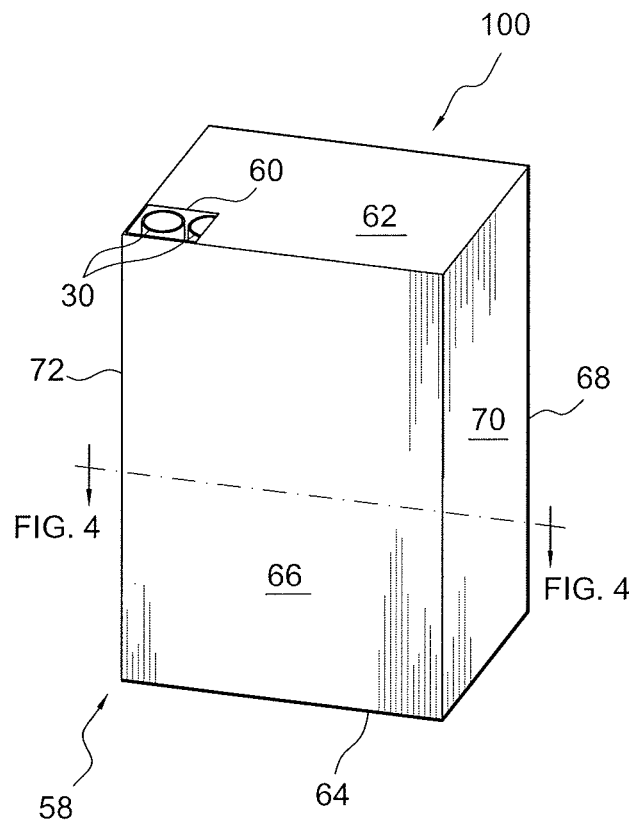
FIG. 3 illustrates a storage container of an exemplary temperature measurement system.
Figure 4:
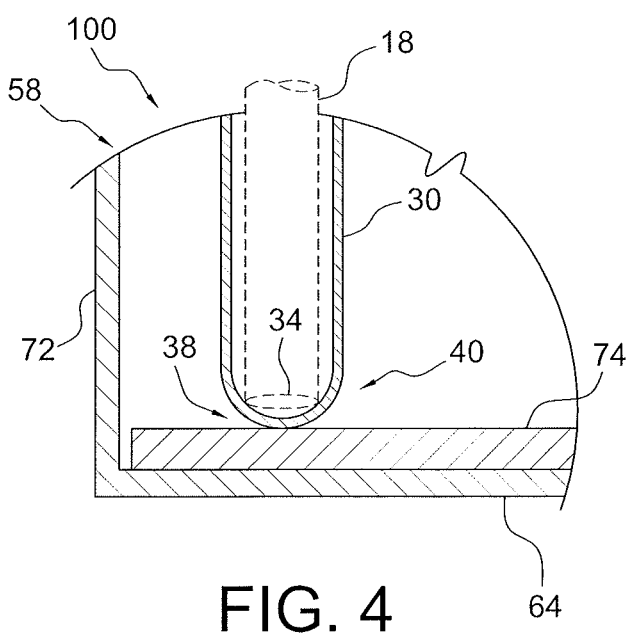
FIG. 4 is a cutaway view of a portion of the storage container shown in FIG. 3.

As shown in FIG. 3, the storage container 58 may include, for example, a front 66, a back 68, and at least two sides 70, 72. In additional exemplary embodiments, it is understood that the storage container 58 may include additional sides and/or other structures, depending upon, for example, the configuration of the probe covers 30 and/or storage requirements related to the probe covers 30. As shown in FIG. 3, an exemplary storage container 58 may also include a top 62 and a bottom wall 64 disposed opposite the top 62. The front 66, back 68, and at least two sides 70, 72 may be disposed orthogonal to the bottom wall 64. In an exemplary embodiment, the top 62 may define at least a portion of the opening 60. In additional exemplary embodiments, at least a portion of the top 62 may be removed to expose the opening 60, and in further exemplary embodiments, substantially the entire top 62 may be removed from the storage container 58. In such exemplary embodiments, substantially all of the probe covers 30 disposed within the storage container 58 may be exposed for removal.

As can be seen via the opening 60 illustrated in FIG. 3, two or more probe covers 30 may be positioned adjacently within the storage container 58. For example, two or more such probe covers 30 may be substantially aligned along respective lengths thereof within the storage container 58. In such exemplary embodiments, a plurality of probe covers 30 may be supported by, for example, the bottom wall 64 of the storage container 58, and may be arranged to stand within the storage container 58 on the respective distal ends 40 thereof.

As shown in FIG. 4, the conductor 74 described above may be disposed on the bottom wall 64 of the storage container 58, and the distal end 40 of each respective probe cover 30 disposed within the storage container 58 may be in contact with the conductor 74. In exemplary embodiments, the conductor 74 may extend along the bottom wall 64 from the front 66 to the back 68 of the storage container 58. The conductor 74 may also extend from the first side 70 to the second side 72 such that the conductor 74 covers substantially the entire bottom wall 64. Although FIG. 4 illustrates the conductor 74 being disposed on an inner surface of the bottom wall 64, in additional exemplary embodiments, the conductor 74 may be disposed on an outer surface of the bottom wall 64. As discussed above, in still further exemplary embodiments, the conductor 74 may be formed integrally with the bottom wall 64.

As shown in at least FIG. 4, when the shaft 18 is disposed within the probe cover 30 such that a capacitance sensor 34 is disposed adjacent to and/or in contact with the tip 38 of the probe cover 30, the capacitance sensor 34 may be configured to measure a change in capacitance resulting from the capacitance sensor 34 being separated from the conductor 74 by the probe cover 30. For instance, the capacitance measured by the capacitance sensor 34 when disposed as shown in FIG. 4 may be different than a capacitance measured if the capacitance sensor 34 of FIG. 4 was disposed in direct contact with the conductor 74 on the bottom wall 64. Although not described in greater detail herein, in further exemplary embodiments the capacitance sensor 34 may be configured to measure a change in capacitance caused by relative movement between the capacitance sensor 34 and the conductor 74.

The temperature probes 10, probe covers 30, and storage containers 58 described herein may be utilized by physicians, nurses, and/or other healthcare professionals in a variety of different environments. For example, the devices and/or the temperature measurement systems 100, 200, 300 described herein may be employed in any of a number of examination facilities to determine one or more temperatures associated with a patient, such as, for example, a core temperature of the patient. Such a temperature determination may be utilized by the healthcare professional to assist in treating the patient, and may have a variety of uses that are well known in the medical field.

For example, the user may insert at least a portion of the temperature probe 10, such as the shaft 18, into the probe cover 30 via the orifice 46. In an exemplary embodiment, the probe cover 30 may be disposed within a storage container 58 while the shaft 18 of the temperature probe 10 is inserted into the probe cover 30. In such an exemplary embodiment, the probe cover 30 may be accessed through the opening 60 of the storage container 58 for insertion of the shaft 18. In such an exemplary embodiment, the temperature probe 10 may be moved in the direction of arrow 50 (FIG. 1) relative to the probe cover 30 for insertion. Alternatively, in exemplary embodiments in which the probe cover 30 has been removed from the storage container 58 before connection with the temperature probe 10, the probe cover 30 may be moved in the direction of arrow 48 (FIG. 1) relative to the temperature probe 10 to facilitate a connection with the temperature probe 10.

As one or more of the retention components 27 of the temperature probe 10 come into contact with the probe cover 30, such retention components 27 may hook, clip, and/or otherwise mate with the proximal end 42 of the probe cover 30 to assist in retaining the probe cover 30 on the shaft 18. In exemplary embodiments in which the proximal end 42 of the probe cover 30 defines one or more of the notches, cutouts, and/or other retention components described above, the retention components of the probe cover 30 may communicate with the retention components 27 of the temperature probe 10 to assist in retaining the probe cover 30 thereon.

For example, the user may dispose the shaft 18 within the probe cover 30 such that a capacitance sensor 34 disposed proximate the distal end 15 of the shaft 18 is positioned proximate the distal end 40 of the probe cover 30. The shaft 18, along with the probe cover 30, may then be disposed within a body cavity and/or proximate to any other like measurement site of the patient, and the capacitance sensor 34 may be activated to measure and/or otherwise determine a first capacitance and/or a first change in capacitance associated with the body cavity and/or other measurement site. In such an exemplary embodiment, the body cavity and/or measurement site may constitute a conductor 74, and a virtual capacitor may be formed by the capacitance sensor 34 and the body cavity and/or measurement site.

Figure 2:
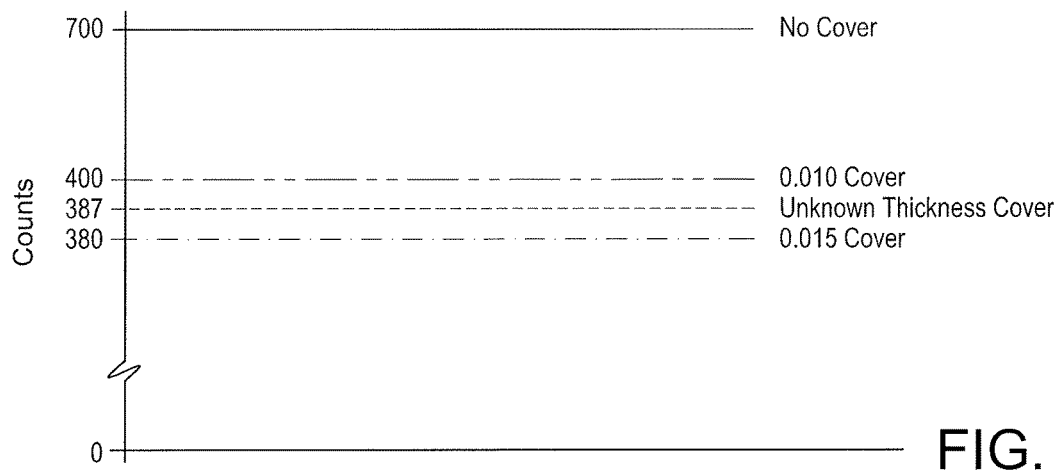
FIG. 2 illustrates a capacitance plot according to an exemplary embodiment of the present disclosure.
Figure 10:
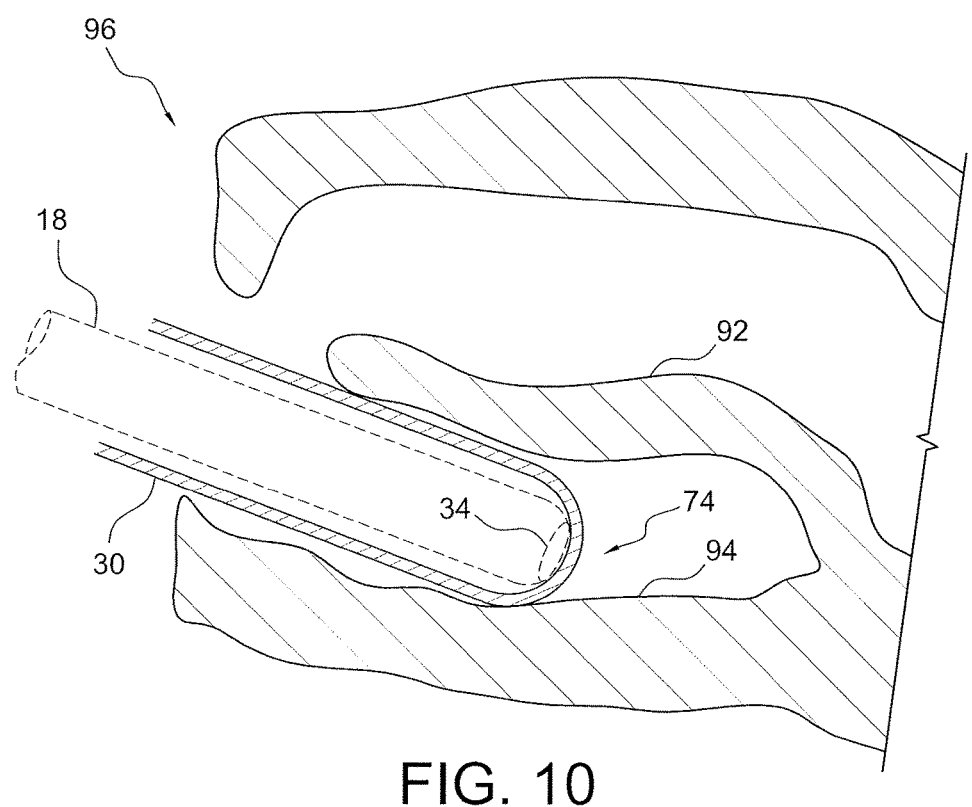
FIG. 10 illustrates a partial view of a mouth of a patient according to an exemplary embodiment of the present disclosure.

For example, FIG. 2 illustrates an exemplary capacitance plot corresponding to an embodiment of the temperature measurement system 100, 200 in which a capacitance sensor 34 is disposed proximate the distal end 15 of the shaft 18, and the conductor 74 comprises a body cavity and/or other like measurement site of the patient. An exemplary embodiment in which the conductor 74 comprises a body cavity and/or other measurement site of the patient, such as, for example, a mouth 96 of the patient is illustrated in FIG. 10. In the exemplary embodiment shown in FIG. 10, the probe cover 30 may be disposed in contact with, for example, the tongue 92, and/or an internal mouth surface 94 of the patient. In such exemplary embodiments, the tongue 92 and/or the mouth surface 94 may comprise the conductor 74.

As shown in FIG. 2, one or more known and/or reference capacitance values may be stored in the memory of the controller 52. Such values may correspond to, for example, a capacitance sensed without a probe cover 30 being disposed on the shaft 18 and the capacitance sensor 34 being in direct contact with the conductor 74 (e.g., 700 counts), a capacitance sensed with a reference probe cover 30 having a thickness of 0.010 inches disposed on the shaft 18 (e.g., 400 counts), and a capacitance sensed with a reference probe cover 30 having a thickness of 0.015 inches disposed on the shaft 18 (e.g., 380 counts). It is understood that the reference capacitance values corresponding to the 0.010-inch and 0.015-inch probe covers 30 may vary depending on, for example, the type of conductor 74, the location of the capacitance sensor 34 relative to the probe cover 30, the location of the capacitance sensor 34 relative to the conductor 74, and/or other factors related to the particular configuration of the temperature measurement system 100.

In the exemplary core temperature determination described above with respect to FIG. 2, if the first capacitance determined by the capacitance sensor 34 corresponds to a capacitance value of 387 counts, the controller 52 may determine a difference between the first capacitance and one of the stored reference capacitance values to determine an unknown thickness of the probe cover 30. For example, the controller 52 may extrapolate between the two reference capacitance values discussed above to determine the thickness of the probe cover 30 used during measurement of the first capacitance. In alternative exemplary embodiments, the controller 52 may use any other known mathematical and/or functional relationships to determine the thickness of the probe cover 30, and in further exemplary embodiments, the controller 52 may use one or more stored look-up tables to determine such a thickness. This determined thickness may be used by the controller 52 as an input to a core temperature determination algorithm. For example, the controller 52 may determine the core temperature of the patient based on the determined thickness of the probe cover 30 being used as well as a temperature of the body cavity as measured by the temperature sensor 32.

Figure 5:
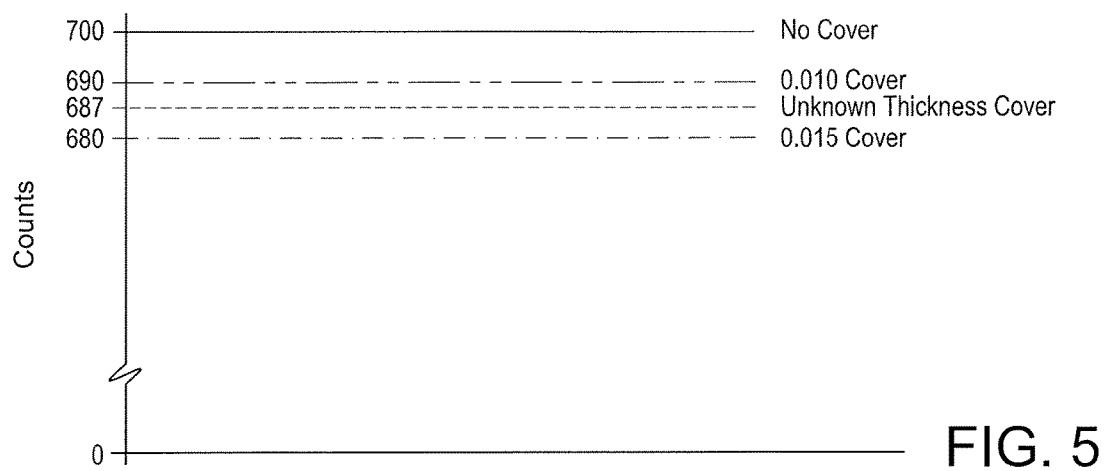
FIG. 5 illustrates a capacitance plot according to another exemplary embodiment of the present disclosure.

While the capacitance plot shown in FIG. 2 is illustrative of an exemplary embodiment, such as the embodiment shown in FIG. 10, in which the body cavity of the patient comprises the conductor 74, in further exemplary core temperature determination methods, a conductor 74 disposed on the bottom wall 64 of the storage container 58 or on the base 86 of a receptacle 84 may be used to measure a change in capacitance. For example, the capacitance plot shown in FIG. 5 is illustrative of the exemplary embodiment of FIG. 4 in which the capacitance sensor 34 is disposed at the tip 16 of the shaft 18, the tip 16 is disposed adjacent to the tip 38 of the probe cover 30, and the distal end 40 of the probe cover 30 is in contact with a conductor 74 disposed on the bottom wall 64 of the storage container 58. In such an exemplary embodiment, the capacitance sensor 34 may be separated from the conductor 74 by the relatively thin probe cover 30, and the capacitance sensor 34 may measure a change in capacitance resulting from the capacitance sensor 34 being separated from the conductor 74 by the distal end 40 of the probe cover 30. As shown in FIG. 5, in such an exemplary embodiment, an exemplary reference capacitance value corresponding to a 0.010-inch probe cover 30 may be 690 counts and an exemplary reference capacitance value corresponding to a 0.015-inch probe cover 30 may be 680 counts. Such reference capacitance values may be higher than, for example, the values discussed above with respect to FIG. 2 due to the type of conductor 74 shown in FIG. 4, and the proximity of the capacitance sensor 34 shown in FIG. 4 to the conductor 74. In the exemplary embodiment of FIGS. 4 and 5, if the first capacitance determined by the capacitance sensor 34 corresponds to a capacitance value of 687 counts, the controller 52 may determine a difference between the first capacitance and one of the stored reference capacitance values to determine an unknown thickness of the probe cover 30. This process may be similar to the methods described above with regard to FIG. 2. Additionally, as described above with respect to FIG. 2, the controller 52 may determine the core temperature of the patient based on the determined thickness of the probe cover 30 as well as a temperature of the body cavity as measured by the temperature sensor 32.

Figure 8:
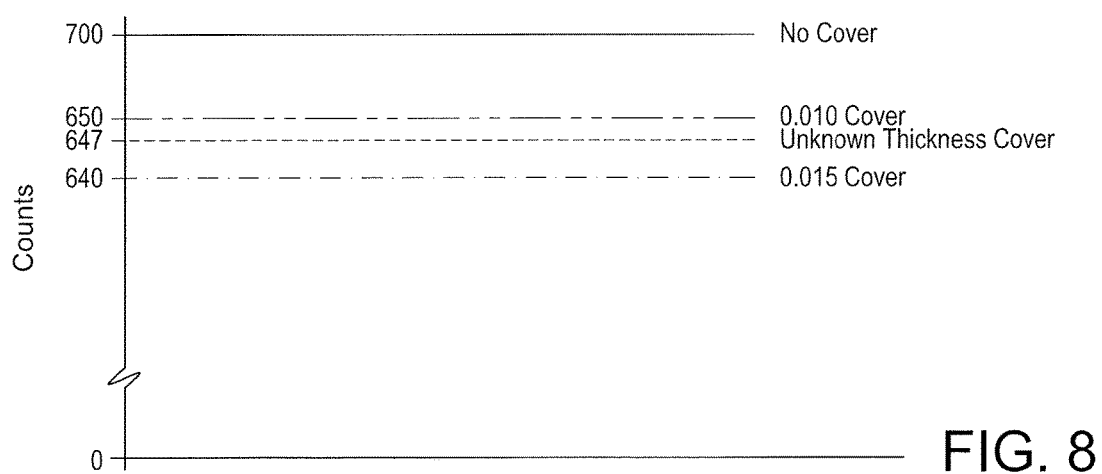
FIG. 8 illustrates a capacitance plot according to a further exemplary embodiment of the present disclosure.

The capacitance plot shown in FIG. 8 is illustrative of the exemplary embodiment of FIG. 7 in which the capacitance sensor 34 is disposed at the tip 16 of the shaft 18, the tip 16 is disposed adjacent to the tip 38 of the probe cover 30, and the distal end 40 of the probe cover 30 is in contact with the bottom wall 64 of the storage container 58. The bottom wall 64 is disposed on the base 86 of the receptacle 84, and the conductor is disposed on the inner surface 88 of the base 86. In this exemplary embodiment, the capacitance sensor 34 is separated from the conductor 74 by the probe cover 30 and the bottom wall 64, and the capacitance sensor 34 may measure a change in capacitance resulting from the capacitance sensor 34 being separated from the conductor 74 by the distal end 40 of the probe cover 30 and the bottom wall 64. As shown in FIG. 8, in such an exemplary embodiment, an exemplary reference capacitance value corresponding to a 0.010-inch probe cover 30 may be 650 counts and an exemplary reference capacitance value corresponding to a 0.015-inch probe cover 30 may be 640 counts. While such reference capacitance values may be higher than, for example, the values discussed above with respect to FIG. 2, such values may be slightly lower than the values discussed above with respect to FIG. 5 due to the proximity of the capacitance sensor 34 shown in FIG. 7 to the conductor 74. In the exemplary embodiment of FIGS. 7 and 8, if the first capacitance determined by the capacitance sensor 34 corresponds to a capacitance value of 647 counts, the controller 52 may determine a difference between the first capacitance and one of the stored reference capacitance values to determine an unknown thickness of the probe cover 30. This process may be similar to the methods described above with regard to FIG. 2. Additionally, as described above with respect to FIG. 2, the controller 52 may determine the core temperature of the patient based on the determined thickness of the probe cover 30 as well as a temperature of the body cavity as measured by the temperature sensor 32.

In additional exemplary core temperature determination methods, a conductor 74 disposed at a proximal end of the shaft 18 may be used to measure a change in capacitance. For example, the capacitance plot shown in FIG. 5 may also be illustrative of the exemplary embodiment of FIG. 9 in which the capacitance sensor 34 is disposed proximate the proximal end 13 of the shaft 18, such as on the base 24 of the shaft 18. Additionally, the conductor 74 may be a metallic ring encircling a portion of the proximal end 13. The conductor 74 may overlay a portion of the capacitance sensor 34, and the probe cover 30 may be disposed on the shaft 18 between the capacitance sensor 34 and the conductor. In such an exemplary embodiment, the capacitance sensor 34 may be separated from the conductor 74 by the relatively thin probe cover 30 and an additional gap or clearance provided between the conductor 74 and the probe cover 30 for connection and/or disconnection of the probe cover 30. The capacitance sensor 34 may measure a change in capacitance resulting from the probe cover 30 being disposed between the capacitance sensor 34 and the ring-shaped conductor 74. This process may be similar to the methods described above with regard to FIG. 2. Additionally, as described above with respect to FIG. 2, the controller 52 may determine the core temperature of the patient based on the determined thickness of the probe cover 30 as well as a temperature of the body cavity as measured by the temperature sensor 32.

FIG. 12 illustrates another exemplary capacitance plot corresponding to an embodiment of the temperature measurement system 200 in which a capacitance sensor 34 is disposed proximate the distal end 15 of the shaft 18. One or more additional capacitance sensors 34 may be disposed on the shaft 18 proximal to the capacitance sensor 34 disposed proximate the distal end 15, and such an exemplary temperature measurement system 200 is shown in FIG. 11. Such capacitance sensors 34 may be configured to generate one or more signals indicative of at least one of a proximity to the patient measurement site and an identity of the measurement site. For example, as illustrated by the capacitance plot of FIG. 12, such sensors 34 may be configured to sense a plurality of capacitance values (i.e., values A-J shown in FIG. 12) and/or a plurality of changes in capacitance values, and the signals generated by the capacitance sensors 34 may be indicative of such values. The temperature measurement system 200 of FIG. 12 may be configured to determine a core temperature of the patient based on the one or more such signals generated by sensors 34 as well as signals generated by the temperature sensor 32 indicative of a temperature associated with the measurement site. As described above with respect to FIG. 2, in such embodiments, the measurement site (not shown in FIGS. 11 and 12) may comprise the conductor 74.

As shown in FIG. 12, one or more known and/or reference capacitance values may be stored in the memory of the controller 52. Such values may correspond to, for example, a capacitance sensed without a probe cover 30 being disposed on the shaft 18 and the capacitance sensor 34 being in direct contact with the conductor 74 (e.g., 700 counts). The capacitance sensor 34 may also sense one or more capacitance values (e.g., values A-C) indicative of a change in capacitance once a probe cover 30 has been disposed on the shaft 18. Values A-C may be representative of capacitance values (e.g., 650 counts, 645 counts, and 640 counts, respectively) corresponding to probe covers 30 having various thicknesses. For example, a first capacitance value A may be sensed relative to a conductor 74 while a probe cover 30 having a corresponding first thickness is disposed on the shaft 18. This first value A may be greater than, for example, a second capacitance value B sensed relative to the same conductor 74 while a probe cover 30 having a corresponding second thickness less than the first thickness is disposed on the shaft 18. Accordingly, the controller 52 may be configured to determine whether a probe cover 30 is present on the shaft 18 based on a difference between the capacitance value sensed without a probe cover 30 being disposed on the shaft (e.g., 700 counts) and one of the capacitance values A-C. The controller 52 may also be configured to determine a thickness, configuration, manufacturer, and/or type of probe cover 30 disposed on the shaft 18 based on the variations in capacitance values A-C sensed while the probe cover 30 is on the shaft 18.

With continued reference to FIG. 12, once the probe cover 30 has been disposed on the shaft 18, the one or more capacitance sensors 34 may be configured to determine the proximity to the measurement site as the temperature probe 10 (i.e., the capacitance sensor 34) is moved toward and/or otherwise approaches the measurement site. For example, the capacitance sensor 34 may sense one or more capacitance values (e.g., values D-F) indicative of a change in capacitance as the temperature probe 10 is moved closer to the measurement site and/or any other like conductor 74. Values D-F may be representative of capacitance values (e.g., 600 counts, 595 counts, and 590 counts, respectively) corresponding to decreasing respective distances between the sensor 34 and the measurement site. For example, a first capacitance value D may be sensed relative to the measurement site while the sensor 34 is disposed at a first distance from the measurement site. This first value D may be greater than, for example, a second capacitance value E sensed relative to the same measurement site while the sensor 34 is disposed at a second distance from the measurement site less than the first distance. Accordingly, the controller 52 may be configured to determine a proximity of the temperature probe 10 (i.e., the capacitance sensor 34) to the measurement site based on one or more such values D-F, and such proximity determinations may be made prior to contact between, for example, the shaft 18 and the measurement site.

In exemplary embodiments, the controller 52 may be configured to determine the proximity to the measurement site based on one or more differences between the respective capacitance values D-F and a known capacitance value indicative of the shaft 18, the capacitance sensor 34, and/or the temperature probe 10 being disposed substantially at the measurement site. For example, one or more known capacitance values (e.g., values H-J) indicative of the temperature probe 10 being disposed in contact with different respective measurement sites may be stored in a memory of the controller 52. Values H-J may be representative of known capacitance values (e.g., 445 counts, 440 counts, and 435 counts, respectively) associated with the capacitance sensor 34 being substantially in contact with different measurement sites (e.g., the mouth, the axilla, and the rectum, respectively). In such embodiments, the controller 52 may determine a difference $\Delta_1$ between the value D-E measured as the temperature probe 10 approaches the measurement site and one of the respective known values H-J. The controller 52 may be configured to determine a proximity to the respective measurement site based on such a difference. In such exemplary embodiments, the controller 52 may determine the difference $\Delta_1$ between the value D-E measured as the temperature probe 10 approaches the measurement site and an average of the respective known values H-J.

Once the temperature probe 10 has been disposed substantially at the measurement site, the shaft 18 may be placed into contact with the measurement site. In exemplary embodiments in which the measurement site comprised, for example, the rectum or other like body cavities, a portion of the shaft 18 may be inserted into the measurement site to facilitate temperature determination. In such embodiments, it is understood that a first capacitance sensor 34 disposed on the shaft 18 proximate the tip 16 may determine a first capacitance value indicative of a first depth of insertion of the shaft 18 at the measurement site. A second capacitance sensor 34 disposed on the shaft 18 proximal to the first capacitance sensor 34 may determine a second capacitance value indicative of a second depth of insertion of the shaft 18 at the measurement site. Such sensors 34 may send respective signals indicative of these capacitance values to the controller 52, and the controller 52 may determine a depth of insertion of the shaft 18 based on such signals and/or capacitance values. For example, the controller 52 may determine the depth of insertion based on a difference between such first and second capacitance values. Alternatively, the controller 52 may interpolate between such capacitance values and/or utilize such capacitance values as inputs to one or more insertion depth algorithms in determining the depth of insertion. In further exemplary embodiments, the controller 52 may use one or more stored look-up tables and/or any other known mathematical and/or functional relationships to determine the depth of insertion. It is also understood that similar methods of determining the depth of insertion may be employed in embodiments in which such sensors 34 comprise substantially linear capacitance sensors 34.

With continued reference to FIG. 12, the controller 52 may also be configured to determine the identity of the measurement site based on a correlation between a measured change in capacitance and a known change in capacitance associated with the measurement site of interest. For example, the capacitance sensor 34 may measure a change in capacitance when the temperature probe 10 (i.e., the sensor 34) is disposed substantially at the measurement site. The controller 52 may compare this measured change in capacitance with one or more known changes in capacitance stored in a memory thereof, wherein each known change in capacitance is indicative of a different respective measurement site. The controller 52 may determine the identity of the measurement site in question by finding a strongest correlation (e.g., a smallest difference) between the measured change in capacitance and the known changes in capacitance.

As shown in FIG. 12, in such embodiments the capacitance sensor 34 may be configured to determine a capacitance value G associated with the measurement site in question. The controller 52 may be configured to determine a difference between such a value G and a plurality of known capacitance values, such as values H-J representative of known capacitance values associated with the capacitance sensor 34 being substantially in contact with different measurement sites. In such embodiments, the controller 52 may determine a difference $\Delta_2$ between the value G measured while the temperature probe 10 is disposed substantially at the measurement site and one of the respective known values H-J associated with the respective potential measurement site of the patient. The controller 52 may be configured to determine the identity of the respective measurement site based on such a difference. For example, the controller may select one of the respective potential measurement sites corresponding to a smallest determined difference $\Delta_2$ between the value G and each of the known values H-J. Alternatively, the controller 52 may interpolate between such capacitance values and/or utilize such capacitance values as inputs to one or more measurement site identity algorithms in determining the identity of the measurement site. In further exemplary embodiments, the controller 52 may use one or more stored look-up tables and/or any other known mathematical and/or functional relationships to determine the identity of the measurement site. In further exemplary embodiments, the controller 52 may be configured to determine whether the temperature probe 10 is properly positioned at the measurement site. For example, before or after determining the identity of the measurement site, the controller 52 may be configured to evaluate the value G, measured while the temperature probe 10 is disposed substantially at the measurement site, to determine whether the proximity between the measurement site and the shaft 18 and/or the capacitance sensor 34 is sufficient for accurate temperature measurements. In such embodiments, the controller 52 may evaluate the value G to determine whether the proximity between the measurement site and the shaft 18 and/or the capacitance sensor 34 is sufficient for accurate temperature measurements. If the controller 52 determines that the temperature probe 10 is not properly positioned at the measurement site, the controller 52 may inform the user of such a determination via the display 54.

In still further exemplary embodiments, the controller 52 may be configured to automatically select one or more temperature determination algorithms, modes of operation, and/or other like temperature probe control programs for use in determining the core temperature of the patient, and this automatic selection may be based on the measurement site determination. For example, in any of the embodiments described herein, upon determining the identity of the measurement site, the controller 52 may select and/or activate one or more stored algorithms associated with the determined measurement site. Such algorithms may be tuned and/or otherwise particularly tailored for use when the temperature probe 10 is disposed at the associated measurement site. Thus, selecting and/or using such tailored algorithms in response to determining the identity of the measurement site may increase the accuracy of the core temperature determination.

FIGS. 14 and 15 illustrate exemplary voltage plots corresponding to a further embodiment of the temperature measurement system 300 in which an optical sensor 35 is disposed proximate the distal end 15 of the shaft 18. One or more additional optical sensors 35 may be disposed on the shaft 18 proximal to the optical sensor 35 disposed proximate the distal end 15, and such an exemplary temperature measurement system 300 is shown in FIG. 13. Such optical sensors 35 may be configured to generate one or more signals indicative of at least one of a proximity to the patient measurement site and an identity of the measurement site. For example, such sensors 35 may be configured to sense a plurality of values indicative of an amount of radiation received by the sensor 35, and/or a plurality of values indicative of a change in the amount of radiation received thereby, and the signals generated by the optical sensors 35 may be indicative of such values. Each such value may correspond to a unique respective voltage, and such exemplary voltages L-U are illustrated in the voltage plot of FIG. 14. The temperature measurement system 300 of FIG. 13 may be configured to determine a core temperature of the patient based on the one or more such signals generated by sensors 35 as well as signals generated by the temperature sensor 32 indicative of a temperature associated with the measurement site. In practice, the operation of system 300 shown in FIG. 13 may be substantially similar to the operation of system 200 described above with respect to FIGS. 11 and 12. Accordingly, a summary of the operation of system 300 shall be described below with reference to the voltage plots of FIGS. 14 and 15.

As shown in FIG. 14, one or more known and/or reference voltages may be stored in the memory of the controller 52. Such voltages may correspond to, for example, an amount of radiation, such as visible light, sensed and/or received by the respective optical sensor 35 without a probe cover 30 being disposed on the shaft 18 and the optical sensor 35 being exposed to ambient conditions (e.g., 1.0 volt). The optical sensor 35 may also sense an amount of radiation and/or a change in the amount of radiation received by the sensor 35 once a probe cover 30 has been disposed on the shaft 18. Voltages L-N may be representative of and/or may otherwise correspond to such amounts of radiation and/or changes in the amount of radiation received by the sensor 35. Each voltage L-N may correspond to a respective probe cover 30 having a unique thickness, opacity, and/or other like identifiable characteristic. For example, a first amount of radiation corresponding to a voltage L may be sensed while a probe cover 30 having a corresponding first thickness, opacity, and/or other like identifiable characteristic is disposed on the shaft 18. This first voltage L may be greater than, for example, a second voltage M corresponding to an amount of radiation received by the sensor 35 while a probe cover 30 having a corresponding second thickness, opacity, and/or other like characteristic less than the first characteristic is disposed on the shaft 18. Accordingly, the controller 52 may be configured to determine whether a probe cover 30 is present on the shaft 18 based on a difference between a voltage corresponding to the amount of radiation sensed without a probe cover 30 being disposed on the shaft (e.g., 1.0 volt) and one of the voltages L-N. In exemplary embodiments, while determining whether a probe cover 30 is present on the shaft 18, at least one of the optical sensors 35 may be disposed beneath the probe cover 30 when the probe cover 30 is disposed on the shaft 18, and at least one sensor 35 may be exposed to ambient conditions outside of the probe cover 30 when the probe cover 30 is disposed on the shaft 18. The controller 52 may also be configured to determine a thickness, configuration, manufacturer, and/or type of probe cover 30 disposed on the shaft 18 based on the particular voltage L-N sensed while the probe cover 30 is on the shaft 18.

With continued reference to FIG. 14, once the probe cover 30 has been disposed on the shaft 18, the one or more optical sensors 35 may be configured to determine the proximity to the measurement site as the temperature probe 10 (i.e., the optical sensor 35) is moved toward and/or otherwise approaches the measurement site. For example, the optical sensor 35 may sense values indicative of an amount of radiation received and/or a change in the amount of radiation received as the temperature probe 10 approaches the measurement site. The exemplary voltages O-Q shown in FIG. 14 correspond to amounts of light and/or changes in the amount of light received by the sensor 35 as the distance between the sensor 35 and the measurement site decreases. For example, a first voltage O may be indicative of an amount of radiation sensed while the sensor 35 is disposed at a first distance from the measurement site. This first voltage O may be greater than, for example, a second voltage P sensed while the sensor 35 is disposed at a second distance from the measurement site less than the first distance. Accordingly, the controller 52 may be configured to determine a proximity of the temperature probe 10 (i.e., the optical sensor 35) to the measurement site based on one or more such values O-Q, and such proximity determinations may be made prior to contact between, for example, the shaft 18 and the measurement site.

In exemplary embodiments, the controller 52 may be configured to determine the proximity to the measurement site based on one or more differences between the respective voltages O-Q and a known voltage indicative of the shaft 18, the optical sensor 35, and/or the temperature probe 10 being disposed substantially at the measurement site. For example, one or more known voltages (e.g., S-U) indicative of an amount of radiation and/or a change in an amount of radiation received by the sensor 35 when the temperature probe 10 is disposed in contact with different respective measurement sites may be stored in a memory of the controller 52. Voltages S-U may be associated with the optical sensor 35 being substantially in contact with different respective measurement sites (e.g., the mouth, the axilla, and the rectum, respectively). In such embodiments, the controller 52 may determine a difference $\Delta_3$ between the voltage O-Q and one of the respective known voltages S-U. The controller 52 may be configured to determine a proximity to the respective measurement site based on such a difference. In such exemplary embodiments, the controller 52 may determine the difference $\Delta_3$ between the voltage O-Q associated with the temperature probe 10 approaching the measurement site and an average of the respective known voltages S-U.

Once the temperature probe 10 has been disposed substantially at the measurement site, a portion of the shaft 18 may be inserted into the measurement site to facilitate temperature determination. In such embodiments, a first optical sensor 35 disposed on the shaft 18 proximate the tip 16 may sense a first amount of radiation indicative of a first depth of insertion of the shaft 18 at the measurement site. A second optical sensor 35 disposed on the shaft 18 proximal to the first optical sensor 35 may sense a second amount of radiation indicative of a second depth of insertion of the shaft 18 at the measurement site. Such sensors 35 may send respective signals indicative of these radiation amounts to the controller 52, and the controller 52 may determine a depth of insertion of the shaft 18 based on such signals and/or voltages corresponding to values indicative of the sensed amounts of radiation. Any similar depth algorithms, look-up tables, and/or other known mathematical and/or functional relationships described above with respect to FIG. 12 may be used to determine the depth of insertion.

With continued reference to FIG. 14, the controller 52 may also be configured to determine the identity of the measurement site based on a correlation between a measured amount of radiation and/or change in the amount of radiation received by the optical sensor 35 and a known amount and/or change in the amount of radiation associated with the particular measurement site of interest. For example, the optical sensor 35 may be configured to determine a value indicative of an amount of light and/or other radiation received when the optical sensor 35 is disposed at the measurement site. The exemplary voltage R shown in FIG. 14 may correspond to such a value. The controller 52 may be configured to determine a difference between such a value and a plurality of known values associated with a respective potential measurement site of the patient. Such known values may be represented by the voltages S-U described above, and such voltages S-U may be representative of known voltages associated with the optical sensor 35 being substantially in contact with different measurement sites. In such embodiments, the controller 52 may determine a difference $\Delta_4$ between, for example, the value indicative of the amount of radiation received when the optical sensor 35 is disposed at the measurement site and one of the respective known values associated with the respective potential measurement site of the patient. For example, the controller 52 may determine the difference $\Delta_4$ between the voltage R and one of the voltages S-U. The controller 52 may be configured to determine the identity of the respective measurement site based on such a difference. For example, the controller 52 may select one of the respective potential measurement sites corresponding to a smallest determined difference $\Delta_4$. Alternatively, the controller 52 may utilize a measurement site identity algorithm, look-up table, and/or any other mathematical and/or functional relationship similar to that described above with respect to FIG. 12 to determine the identity of the measurement site. It is also understood that the controller 52 may utilize the voltage R, and/or its corresponding value indicative of an amount of light and/or other radiation received, to assist in determining whether the temperature probe 10 is properly positioned at the measurement site. For example, similar to the process described above with respect to FIG. 12, before or after determining the identity of the measurement site, the controller 52 may be configured to evaluate the value R, measured while the temperature probe 10 is disposed substantially at the measurement site, to determine whether the proximity between the measurement site and the shaft 18 and/or the optical sensor 35 is sufficient for accurate measurements. If, based on this analysis, the controller 52 determines that the temperature probe 10 is not properly positioned at the measurement site, the controller 52 may inform the user of such a determination via the display 54.

Further, the voltage plot of FIG. 15 illustrates a plurality of voltages and changes in voltages corresponding to amounts of radiation received by the optical sensor 35 during use. In particular, as the shaft 18 is inserted into a probe cover 30 disposed within a storage container 58 of the present disclosure, the sensor 35 may determine a first change in the amount of radiation received by the sensor 35. This first change in radiation received, represented by $\Delta_5$ shown in FIG. 15, may result from, for example, the shaft 18 being inserted into the probe cover 30 while the probe cover 30 is disposed within the storage container 58. Accordingly, the first change in radiation received $\Delta_5$ may result from a change in operating conditions where the sensor 35 transitions from receiving unobstructed ambient light with no cover disposed on the shaft 18 to receiving minimal amounts of light within the storage container 58.

Once the shaft 18 is removed from the storage container 58 with the probe cover 30 disposed on the shaft 18, the sensor 35 may measure a second change in radiation received $\Delta_6$. This second change in radiation received $\Delta_6$ may correspond to an increase in the amount of radiation received by the sensor 35. In particular, the second change in radiation received $\Delta_6$ may result from a change in operating conditions in which the sensor 35 transitions from receiving minimal amounts of light within the storage container 58 to receiving ambient light through the probe cover 30 outside of the storage container 58.

As the sensor 35 is disposed at the measurement site, the sensor 35 may measure a third change in radiation received $\Delta_7$. This third change in radiation received $\Delta_7$ may correspond to a decrease in the amount of radiation received by the sensor 35. In particular, the third change in radiation received $\Delta_7$ may result from a change in operating conditions in which the sensor 35 transitions from receiving minimal amounts of light within the storage container 58 to receiving relatively high amounts of ambient light through the probe cover 30 outside of the storage container 58 to receiving reduced amounts of ambient light at the measurement site. For example, in embodiments in which a portion of the shaft 18 is disposed within the mouth, axilla, rectum, and/or other like body cavity, the amount of ambient light received by the sensor 35 may be greatly reduced. In exemplary embodiments, the controller 52 may determine a core temperature of the patient based on a temperature associated with the measurement site, measured by the temperature sensor 32, and at least one of the first, second, and third changes in radiation $\Delta_5$, $\Delta_6$, $\Delta_7$ described above. Further, it is understood that the core temperature determination methods described herein with respect to FIG. 15 may be combined, in whole or in part, with one or more of the processes described above with respect to FIGS. 12 and 14.

In the exemplary core temperature determination methods described herein, the sensor 32 may be activated to sense a temperature of the body cavity while the shaft 18 is disposed within the body cavity and/or at any other like measurement site of the patient. For example, in an embodiment in which the first sensor 32 comprises a thermocouple and/or a thermistor, the first sensor 32 may be utilized to measure the temperature of the body cavity. Further, in any of the exemplary embodiments described herein, sensing the body cavity temperature may be sensed by activating one or more infrared temperature sensors of the temperature probe 10, such as one or more of the thermopiles described above.

Signals indicative of the measured change in capacitance, the measured change in the amount of radiation received, and/or the measured body cavity temperature may be sent to the controller 52 by the various sensors 32, 34, 35 described herein, and the controller 52 may assist in determining the core temperature based on such parameters. For example, determining the thickness of the probe cover 30 based on the sensed capacitance change may assist in accurately determining such a core temperature. In exemplary embodiments, such capacitance and a corresponding thickness of the probe cover 30 may be utilized in the core temperature calculation to reduce error. In further exemplary embodiments, the determined proximity to the measurement site, identity of the measurement site, and/or probe cover type may also be utilized in the core temperature determination to further reduce error. Such error is commonly caused by using an inaccurate estimate of probe cover thickness and a corresponding inaccurate effect of such thickness on the measured body cavity temperature. It is understood that even small discrepancies between the actual and estimated probe cover thickness may have a dramatic effect on the resulting core temperature determined by the controller 52. It is also understood that incorporating information associated with the determined proximity to the measurement site, identity of the measurement site, and/or probe cover type may enhance the accuracy and reliability of the core temperature determination, and may further reduce such error.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A medical device, comprising:
 a first sensor configured to:
  determine a change in an amount of radiation received by the first sensor as the first sensor approaches a measurement site, and generate a first signal indicative of the change in the amount of radiation;
a second sensor configured to generate a second signal indicative of a temperature associated with the measurement site; and
a controller in communication with the first sensor and the second sensor, the controller configured to:
receive the first signal,
receive the second signal,
determine an identity of the measurement site based at least in part on the change in the amount of radiation,
select, based on the identity of the measurement site, an operating mode of the medical device associated with estimating a core temperature of a patient based on the second signal; and
based on the selecting, cause the medical device to operate in the operating mode.

2. The medical device of claim 1, wherein the identity of the measurement site is selected from a group consisting of a mouth, an axilla, a rectum, and an ear drum.

3. The medical device of claim 1, wherein
the first sensor comprises an optical sensor in communication with the controller, and
determining the identity of the measurement site includes converting, with the controller, the first signal into at least one voltage value representative of the change in the amount of radiation.

4. The medical device of claim 1, wherein the first sensor comprises a photodiode configured to determine a change in an amount of light received by the photodiode,
the first signal being indicative of the change in the amount of light.

5. The medical device of claim 1, wherein the medical device includes a shaft, and the first sensor comprises
a first photodiode disposed proximate a distal end of the shaft, and
a second photodiode disposed proximal to the first photodiode,
the controller being configured to determine the presence of a probe cover at least partly disposed on the shaft based on a difference between a first amount of light received by the first photodiode and a second amount of light received by the second photodiode.

6. The medical device of claim 5, wherein the first photodiode is disposed beneath the probe cover when the probe cover is at least partly disposed on the shaft, and the second photodiode is exposed to ambient conditions outside of the probe cover when the probe cover is at least partly disposed on the shaft.

7. The medical device of claim 1, wherein the controller is configured to determine a probe cover type associated with a probe cover at least partly disposed on a shaft of the medical device based on the change in the amount of radiation.

8. The medical device of claim 1, wherein determining the identity of the measurement site comprises
determining a value indicative of an amount of light received by the first sensor at the measurement site,
determining differences between the value indicative of the amount of light received by the first sensor at the measurement site and a plurality of known values, each value of the plurality of known values being associated with a respective potential measurement site of the patient, and
selecting one of the respective potential measurement sites of the patient corresponding to a smallest determined difference.

9. The medical device of claim 1, wherein the controller is configured to determine a proximity to the measurement site based on a difference between a value indicative of an amount of light received by the first sensor and a known value indicative of a shaft of the medical device being disposed substantially at the measurement site.

10. The medical device of claim 1, wherein the first sensor comprises a first sensing device disposed on a shaft of the medical device, and a second sensing device disposed on the shaft proximal to the first sensing device,
the first sensing device being configured to determine a first depth of insertion of the shaft at the measurement site, and the second sensing device being configured to determine a second depth of insertion of the shaft at the measurement site greater than the first depth.

11. A method of manufacturing a medical device, comprising:
providing a shaft having a distal end and a proximal end;
connecting a first sensor to the shaft, the first sensor configured to:
determine a change in an amount of radiation received by the first sensor as the first sensor approaches a measurement site, and
generate a first signal indicative of the change in the amount of radiation;
connecting a second sensor to the shaft, the second sensor configured to generate a second signal indicative of a temperature associated with the measurement site; and
operably connecting the first sensor and the second sensor to a controller, the controller configured to:
receive the first signal,
receive the second signal,
determine an identity of the measurement site based at least in part on the change in the amount of radiation,
select, based on the identity of the measurement site, an operating mode of the medical device associated with estimating a core temperature of a patient based on the second signal, and
based on the selecting, cause the medical device to operate in the operating mode.

12. The method of claim 11, wherein the first sensor comprises a photodiode configured to determine a change in an amount of light received by the photodiode,
the first signal being indicative of the change in the amount of light.

13. The method of claim 11, wherein the first sensor comprises a first photodiode disposed proximate the distal end of the shaft, and a second photodiode disposed proximal to the first photodiode,
the controller being configured to determine the presence of a probe cover at least partly disposed on the shaft based on a difference between a first amount of light received by the first photodiode and a second amount of light received by the second photodiode.

14. The method of claim 11, wherein determining the identity of the measurement site comprises:
determining a value indicative of an amount of light received by the first sensor at the measurement site,
determining differences between the value indicative of the amount of light received by the first sensor at the measurement site and a plurality of known values, each value of the plurality of known values being associated with a respective potential measurement site of the patient, and
selecting one of the respective potential measurement sites of the patient corresponding to a smallest determined difference.

15. The method of claim 11, wherein the first sensor comprises a first sensing device connected to the shaft, and a second sensing device connected the shaft proximal to the first sensing device, the first sensing device being configured to determine a first depth of insertion of the shaft at the measurement site, and the second sensing device being configured to determine a second depth of insertion of the shaft at the measurement site greater than the first depth.

16. A medical device, comprising:

a shaft having a distal end and a proximal end;
a first sensor disposed on the shaft, the first sensor configured to:
  determine a change in an amount of radiation received by the first sensor caused by a probe cover being at least partly disposed on the shaft, and
  generate a first signal indicative of the change in the amount of radiation;
a second sensor disposed on the shaft, the second sensor configured to generate a second signal indicative of a temperature associated with the measurement site; and
a controller in communication with the first sensor and the second sensor, the controller configured to:
  receive the first signal,
  receive the second signal,
  determine a thickness of the probe cover based at least in part on the change in the amount of radiation indicated by the first signal,
  select an operating mode of the medical device, the operating mode being configured for use in estimating a core temperature of a patient, with the probe cover disposed on the shaft, and based on the second signal, and
  based on the selecting, cause the medical device to operate in the operating mode.

17. The medical device of claim 16, wherein determining the thickness of the probe cover includes determining a probe cover type associated with the probe cover and based at least in part on the change in the amount of radiation.

18. The medical device of claim 16, wherein the controller is configured to determine the thickness of the probe cover based on a difference between a first value indicating a first amount of light received by the first sensor while the first sensor is exposed to ambient conditions, and
a second value indicating a second amount of light received by the first sensor while the probe cover is at least partly disposed on the shaft.

19. The medical device of claim 18, wherein the difference comprises a third value, and the controller is configured to determine the thickness of the probe cover based on a difference between the third value and at least one stored reference value corresponding to a first probe cover having a known thickness.

20. A temperature probe, comprising:

a shaft having a distal end and a proximal end;
a first sensor disposed on the shaft, the first sensor configured to:
  determine a change in an amount of radiation received by the first sensor as the first sensor approaches a measurement site of a patient, and
  generate a first signal indicative of the change in the amount of radiation;
a second sensor disposed on the shaft, the second sensor configured to generate a second signal indicative of a temperature associated with the measurement site of the patient; and
a controller in communication with the first sensor and the second sensor, the controller configured to:
  receive the first signal,
  receive the second signal,
  determine an identity of the measurement site based at least in part on the first signal,
  select, based on the identity of the measurement site, an operating mode of the temperature probe associated with estimating a core temperature of the patient based on the second signal, and
  cause the temperature probe to operate in the operating mode.

* * * * *